(12) United States Patent
Wise et al.

(10) Patent No.: US 12,059,155 B2
(45) Date of Patent: Aug. 13, 2024

(54) STAPLE DRIVER AND GUIDE ASSEMBLY FOR CIRCULAR SURGICAL STAPLER

(71) Applicant: Cilag GmbH International, Zug (CH)

(72) Inventors: Austin E. Wise, Cincinnati, OH (US); Shane R. Adams, Lebanon, OH (US); John S. Kimsey, Walton, KY (US)

(73) Assignee: Cilag GmbH International, Zug (CH)

( * ) Notice: Subject to any disclaimer, the term of this patent is extended or adjusted under 35 U.S.C. 154(b) by 79 days.

(21) Appl. No.: 17/489,877

(22) Filed: Sep. 30, 2021

(65) Prior Publication Data

US 2023/0113766 A1 Apr. 13, 2023

(51) Int. Cl.
| | | |
|---|---|---|
| A61B 17/11 | (2006.01) | |
| A61B 17/115 | (2006.01) | |
| A61B 90/00 | (2016.01) | |
| A61B 17/00 | (2006.01) | |
| A61B 17/34 | (2006.01) | |

(52) U.S. Cl.
CPC .......... *A61B 17/1155* (2013.01); *A61B 90/03* (2016.02); *A61B 2017/00477* (2013.01); *A61B 17/34* (2013.01); *A61B 2090/034* (2016.02)

(58) Field of Classification Search
CPC .................................................. A61B 17/1155
See application file for complete search history.

(56) References Cited

U.S. PATENT DOCUMENTS

| | | | |
|---|---|---|---|
| 5,271,543 A | 12/1993 | Grant et al. | |
| 5,292,053 A | 3/1994 | Bilotti et al. | |
| 5,333,773 A | 8/1994 | Main et al. | |
| 5,350,104 A | 9/1994 | Main et al. | |
| 5,533,661 A | 7/1996 | Main et al. | |
| 8,910,847 B2 | 12/2014 | Nalagatla et al. | |
| 9,713,469 B2 | 7/2017 | Leimbach et al. | |
| 9,907,552 B2 | 3/2018 | Measamer et al. | |
| 9,936,949 B2 | 4/2018 | Measamer et al. | |
| 10,631,866 B2 | 4/2020 | Laurent et al. | |
| 10,667,818 B2 | 6/2020 | McClain et al. | |
| 10,687,819 B2 | 6/2020 | Stokes et al. | |
| 10,709,452 B2 | 7/2020 | DiNardo et al. | |
| 10,874,398 B2 | 12/2020 | Baxter, III et al. | |
| 10,898,187 B2 | 1/2021 | Deck et al. | |

(Continued)

OTHER PUBLICATIONS

International Search Report and Written Opinion dated Dec. 21, 2022 for Application No. PCT/IB2022/059163, 13 pgs.

*Primary Examiner* — Praachi M Pathak
(74) *Attorney, Agent, or Firm* — Frost Brown Todd LLP

(57) ABSTRACT

A surgical stapling instrument includes an anvil defining a plurality of staple forming pockets and a stapling head assembly. The stapling head assembly includes a body, a coupling member capable of actuating the anvil relative to the body, a staple deck defining a plurality of staple openings, and a firing assembly capable of driving a plurality of staples against the staple forming pockets of the anvil. The firing assembly includes a proximal driving body and an array of discrete staple driving segments positioned distal to the proximal driving body. The proximal driving body is slidably housed within the body. The staple driving segments each have a free proximal end. The proximal driving body is capable of simultaneously actuating the array of staple driving segments to drive the plurality of staples against the staple forming pockets of the anvil.

18 Claims, 20 Drawing Sheets

(56) References Cited

U.S. PATENT DOCUMENTS

| | | |
|---|---|---|
| 10,905,419 B2 | 2/2021 | Schings et al. |
| 10,932,781 B2 | 3/2021 | Jones et al. |
| 11,033,266 B2 | 6/2021 | Jones et al. |
| 11,045,193 B2 | 6/2021 | Schings et al. |
| 2013/0087596 A1 | 4/2013 | Fontayne et al. |
| 2015/0083772 A1 | 3/2015 | Miller et al. |
| 2017/0086825 A1* | 3/2017 | Henderson ............. A61B 17/12 |
| 2018/0132849 A1 | 5/2018 | Miller et al. |
| 2019/0200999 A1 | 7/2019 | Tsurimoto et al. |
| 2020/0046353 A1 | 2/2020 | Deck et al. |
| 2021/0038223 A1 | 2/2021 | Schings et al. |

* cited by examiner

STAPLE DRIVER AND GUIDE ASSEMBLY FOR CIRCULAR SURGICAL STAPLER

BACKGROUND

A circular surgical stapler may be used to form an anastomosis between two organ portions of a patient's digestive tract. Examples of circular surgical staplers are described in U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. Patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pat. No. 9,936,949, entitled "Surgical Stapling Instrument with Drive Assembly Having Toggle Features," issued Apr. 10, 2018; U.S. Pat. No. 9,907,552, entitled "Control Features for Motorized Surgical Stapling Instrument," issued Mar. 6, 2018; U.S. Pat. No. 9,713,469, entitled "Surgical Stapler with Rotary Cam Drive," issued Jul. 25, 2017; U.S. Pub. No. 2018/0132849, entitled "Staple Forming Pocket Configurations for Circular Surgical Stapler Anvil," published May 17, 2018; and U.S. Pat. No. 10,709,452, entitled "Methods and Systems for Performing Circular Stapling," issued Jul. 14, 2020. The disclosure of each of the above-cited U.S. Patent Publications and U.S. Patents is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
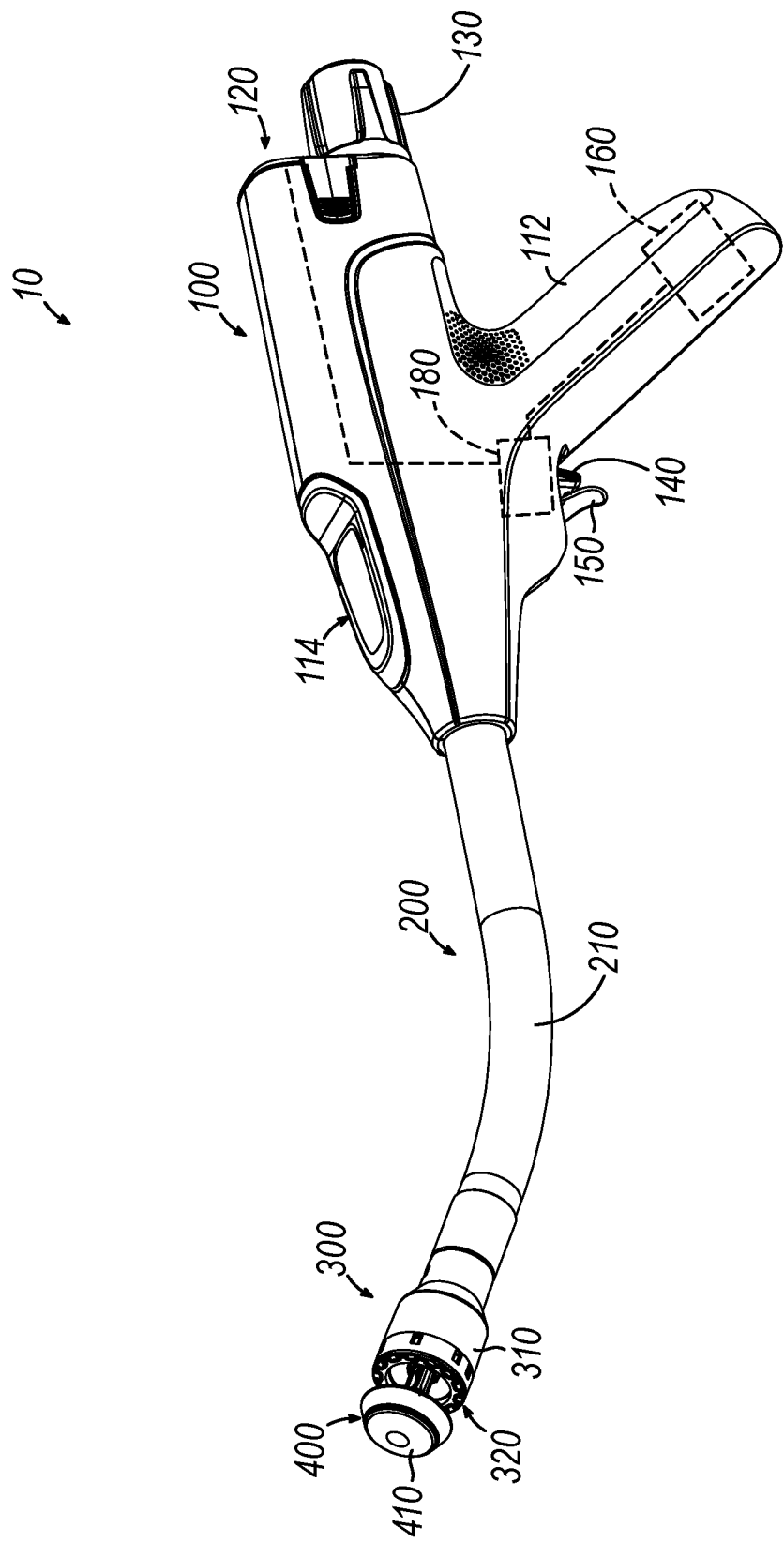
FIG. 1 depicts a perspective view of an exemplary circular surgical stapler that includes a handle assembly, a shaft assembly, and an end effector having a stapling head assembly and an anvil.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose described herein.

I. Overview of Exemplary Circular Surgical Stapling Instrument

Figure 2:
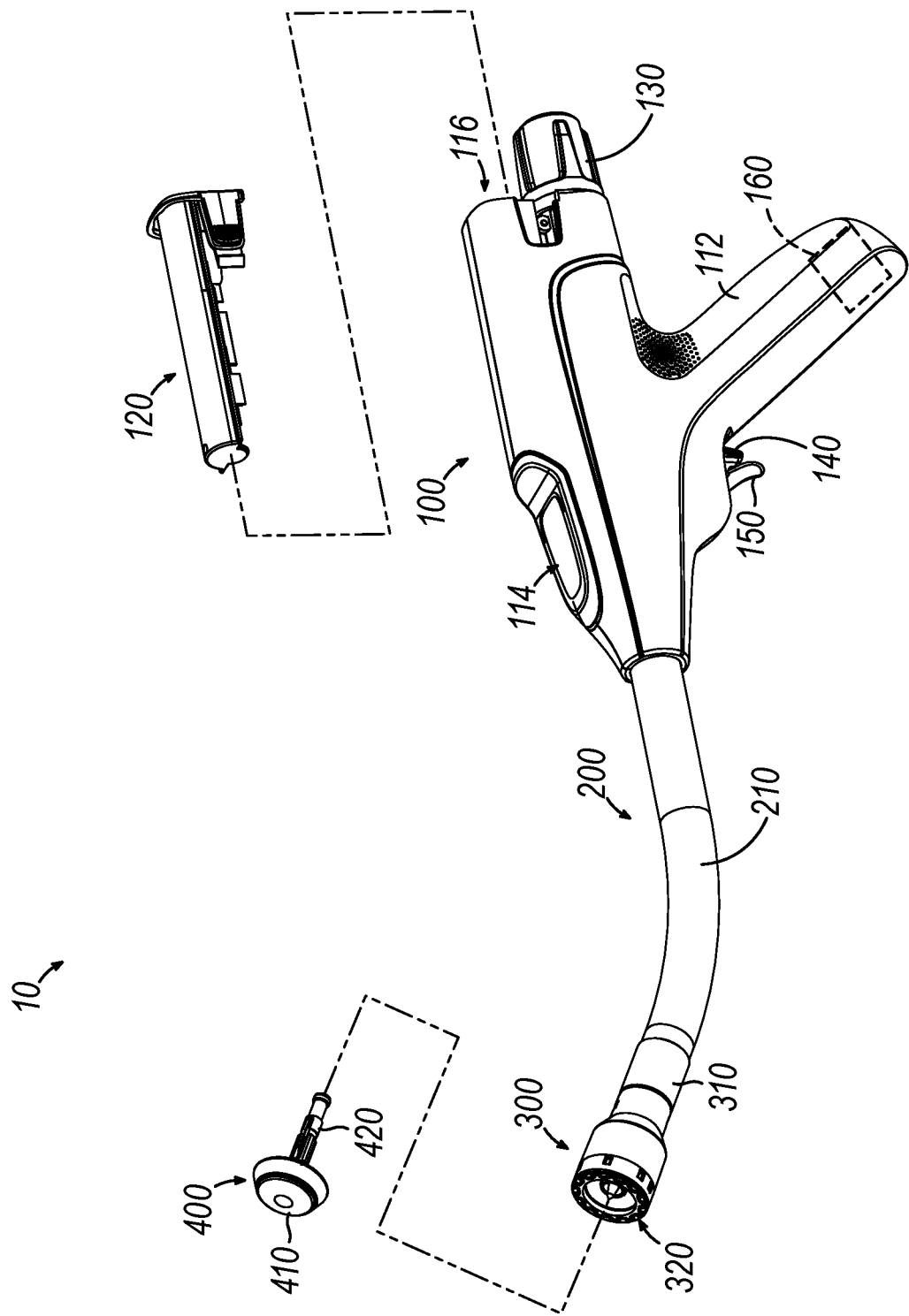
FIG. 2 depicts a perspective view of the circular stapler of FIG. 1, with a battery pack removed from the handle assembly and the anvil separated from the stapling head assembly.

FIGS. 1-2 depict an exemplary circular surgical stapling instrument (10) that may be used to provide an end-to-end, side-to-side, or end-to-side anastomosis between two sections of an anatomical lumen such as a portion of a patient's digestive tract. Instrument (10) of this example includes a body assembly in the form of a handle assembly (100), a shaft assembly (200) extending distally from handle assembly (100), a stapling head assembly (300) at a distal end of shaft assembly (200), and an anvil (400) configured to releasably couple and cooperate with stapling head assembly (300) to clamp, staple, and cut tissue. Instrument (10) further includes a removable battery pack (120) operable to provide electrical power to a motor (160) housed within handle assembly (100), as will be described in greater detail below.

As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A rotatable knob (130) at the proximal end of handle assembly (100) is rotatable to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the clamped tissue.

A. Exemplary Anvil

Figure 3:
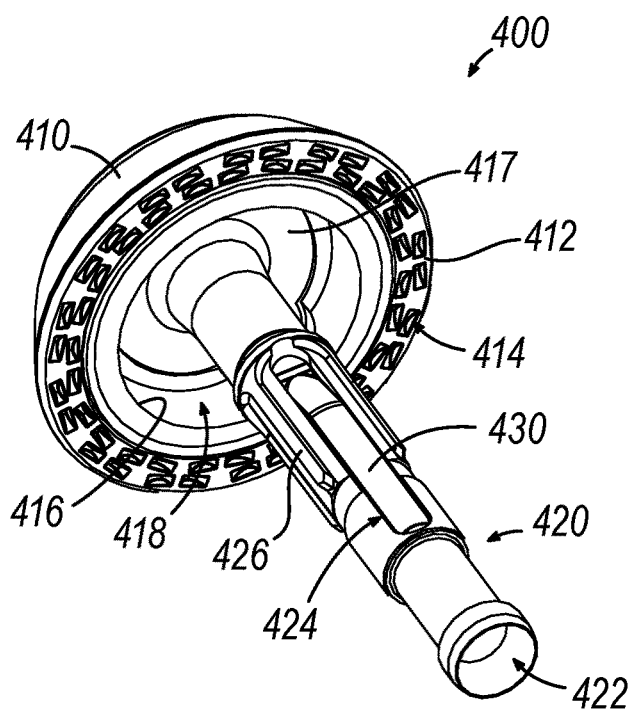
FIG. 3 depicts a perspective view of the anvil of the circular stapler of FIG. 1.

As best seen in FIG. 3, anvil (400) of the present example comprises a head (410) and a shank (420). Head (410) includes a proximal stapling surface (412) that defines a plurality of staple forming pockets (414). Staple forming pockets (414) are arranged in two concentric annular arrays in the present example. Staple forming pockets (414) are configured to deform staples as the staples are driven into staple forming pockets (414). Proximal stapling surface (412) terminates at an inner edge (416), which defines an outer boundary of an annular recess (418) surrounding shank (420). A breakable washer (417) is positioned within annular recess (418) and is configured to provide the operator with a tactile and audible indication that a distal firing stroke has been completed, in addition to serving as a cutting board, as described in greater detail below.

Shank (420) defines a bore (422) and includes a pair of pivoting latch members (430). Latch members (430) are positioned within bore (422) such that distal ends (434) are positioned at the proximal ends of lateral openings (424), which are formed through the sidewall of shank (420). Latch members (430) thus act as retaining clips. This allows anvil (400) to be removably secured to an actuatable closure member in the form of a trocar (330) of stapling head assembly (300), as will be described in greater detail below. Shank (420) of anvil (400) and trocar (330) of stapling head assembly (300) thus cooperate with one another as coupling members. In some versions, stapling head assembly (300) may include an actuatable first coupling feature that is similar in structure to shank (420), and anvil (400) may include a second coupling feature that is similar in structure to trocar (330) and is configured to releasably couple with the first coupling feature.

B. Exemplary Stapling Head Assembly

Figure 4:
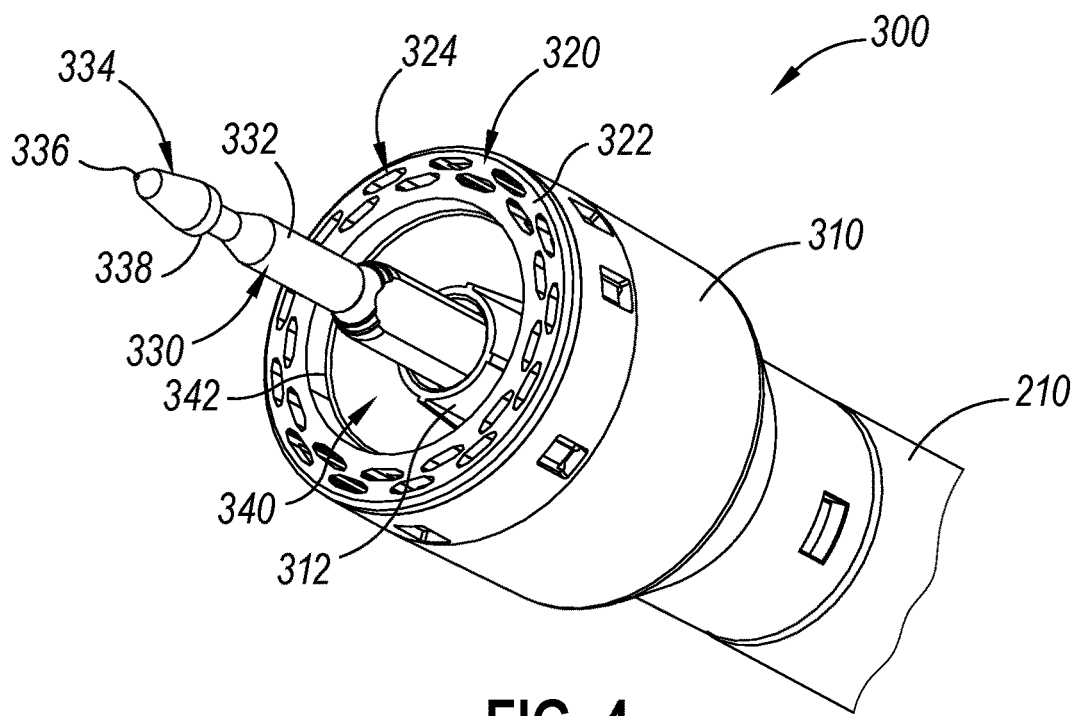
FIG. 4 depicts a perspective view of the stapling head assembly of the circular stapler of FIG. 1.
Figure 5:
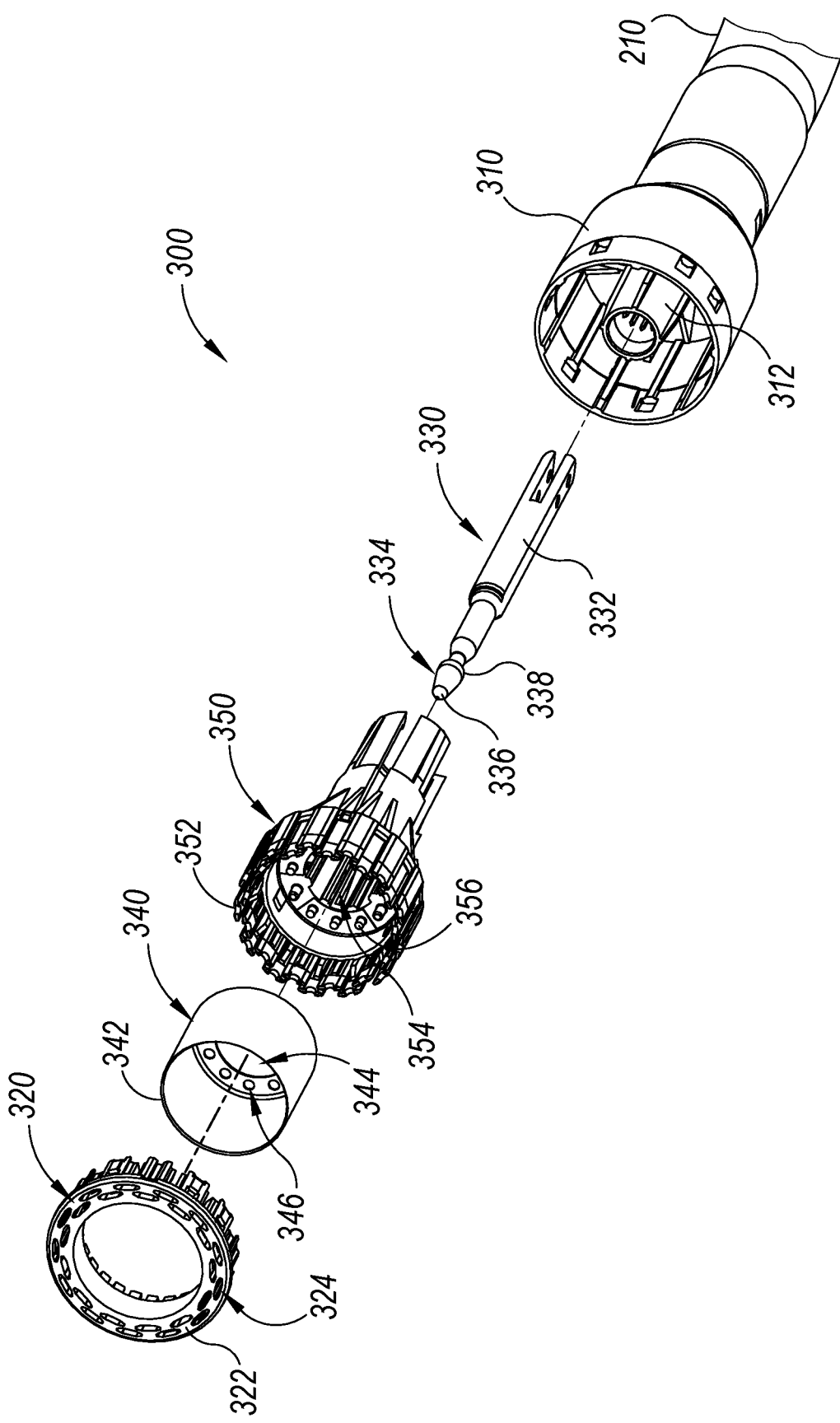
FIG. 5 depicts an exploded perspective view of the stapling head assembly of FIG. 4.

As best seen in FIGS. 4 and 5, stapling head assembly (300) of the present example is coupled to a distal end of shaft assembly (200) and comprises a tubular body member (310) and a staple driver member (350) slidably housed therein. Body member (310) includes a distally extending cylindraceous inner core member (312) positioned coaxially therein. Body member (310) is fixedly secured to an outer sheath (210) of shaft assembly (200), and body member (310) and outer sheath (210) thus serve together as a mechanical ground for stapling head assembly (300).

Trocar (330) is positioned coaxially within inner core member (312) of body member (310). As will be described in greater detail below, trocar (330) is operable to translate distally and proximally relative to body member (310) in response to rotation of knob (130) relative to casing (110) of handle assembly (100). Trocar (330) comprises a shaft (332) and a head (334). Head (334) includes a pointed tip (336) and a radially inwardly extending proximal surface (338). Head (334) and the distal portion of shaft (332) are configured for insertion into bore (422) of anvil (400). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit provided by latch members (430).

Staple driver member (350) is operable to actuate longitudinally within body member (310) in response to activation of motor (160) as will be described in greater detail below. As shown best in FIG. 5, staple driver member (350) of the present example includes two distally presented concentric annular arrays of staple drivers (352). Staple drivers (352) are arranged to correspond with the arrangement of staple forming pockets (414) of anvil (400). Thus, each staple driver (352) is configured to drive a corresponding staple distally into a corresponding staple forming pocket (414) when stapling head assembly (300) is actuated (or "fired"). Staple driver member (350) also defines a bore (354) that is configured to coaxially and slidably receive core member (312) of body member (310). An annular array of studs (356) project distally from a distally presented surface surrounding bore (354).

A cylindraceous knife member (340) is coaxially positioned within a distally-opening central recess of staple driver member (350) that communicates with bore (354). Knife member (340) includes a distally presented, sharp circular cutting edge (342). Knife member (340) is sized such that knife member (340) defines an outer diameter that is just smaller than the diameter defined by the radially inner-most surfaces of the inner annular array of staple drivers (352). Knife member (340) also defines a central opening that is configured to coaxially receive core member (312) of body member (310). An annular array of openings (346) formed in knife member (340) is configured to mate with the annular array of studs (356) of staple driver member (350), such that knife member (340) is fixedly secured to staple driver member (350) via studs (356) and openings (346).

Figure 9:
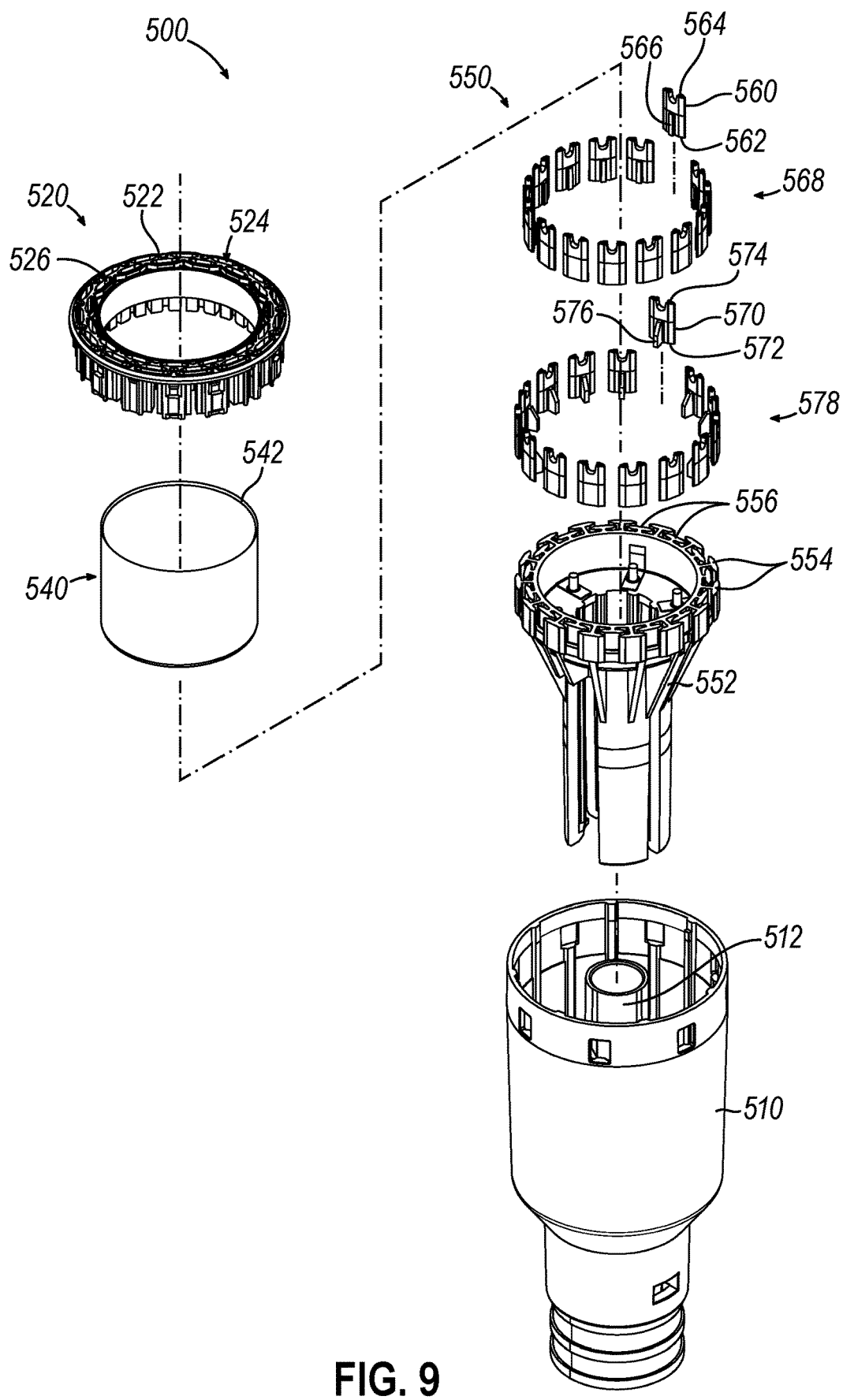
FIG. 9 depicts an exploded perspective view of the staple head assembly of FIG. 8.

An annular deck member (320) is fixedly secured to a distal end of body member (310). Deck member (320) includes a distally presented stapling surface in the form of a deck surface (322) having two concentric annular arrays of staple openings (324). Staple openings (324) are arranged to align with the arrangement of staple drivers (352) of staple driver member (350) and staple forming pockets (414) of anvil (400) described above. Each staple opening (324) is configured to slidably receive and provide a pathway for a corresponding staple driver (352) to drive a corresponding staple distally through deck member (320) and into a corresponding staple forming pocket (414) when stapling head assembly (300) is actuated. As best seen in FIG. 9, deck member (320) has a central opening that defines an inner diameter that is just slightly larger than the outer diameter defined by knife member (340). Deck member (320) is thus configured to permit knife member (340) to translate longitudinally through the central opening concurrently with longitudinal translation of staple driver member (350). In particular, knife member (340) is configured to actuate relative to deck member (340) between a proximal retracted position and a distal extended position, where cutting edge (342) is proximal to deck surface (322) in the proximal retracted position and distal to deck surface (322) in the distal extended position.

C. Exemplary Shaft Assembly

Figure 6:
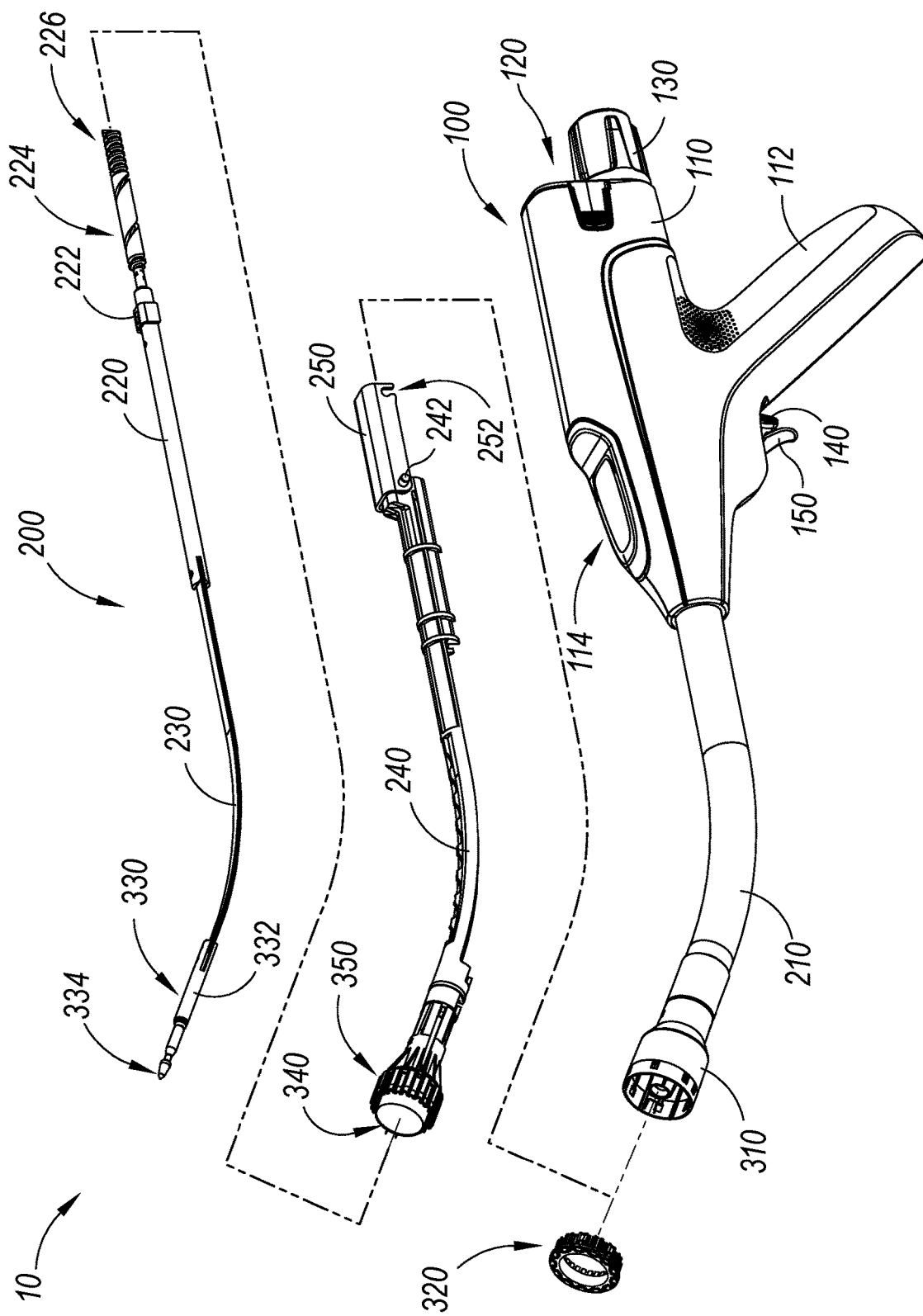
FIG. 6 depicts an exploded perspective view of the circular stapler of FIG. 1, with portions of the shaft assembly shown separated from each other.

FIG. 6 shows various components of shaft assembly (200), which operatively couple components of stapling head assembly (300) with components of handle assembly (100). In particular, and as noted above, shaft assembly (200) includes an outer sheath (210) that extends between handle assembly (100) and body member (310) and includes a medial portion that extends along a curved path.

Shaft assembly (200) further includes a trocar actuation rod (220) having a proximal end operatively coupled with rotatable knob (130) and a distal end coupled with a flexible trocar actuation band assembly (230), the assembly of which is slidably housed within outer sheath (210). The distal end of trocar actuation band assembly (230) is fixedly secured to the proximal end of trocar shaft (332), such that trocar (330) will translate longitudinally relative to outer sheath (210) in response to translation of trocar actuation band assembly (230) and trocar actuation rod (220) relative to outer sheath (210), which occurs in response to rotation of rotatable knob (130). A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a section of coarse helical threading (224) and a section of fine helical threading (226) proximal to coarse helical threading (224), which are configured to control a rate of longitudinal advancement of trocar actuation rod (220), as described in greater detail below.

Shaft assembly (200) further includes a stapling head assembly driver (240) that is slidably housed within outer sheath (210) and about the combination of trocar actuation rod (220) and trocar actuation band assembly (230). Stapling head assembly driver (240) includes a distal end that is fixedly secured to the proximal end of staple driver member (350), a proximal end secured to a drive bracket (250) via a pin (242), and a flexible section disposed therebetween. It should therefore be understood that staple driver member (350) will translate longitudinally relative to outer sheath (210) in response to translation of stapling head assembly driver (240) and drive bracket (250) relative to outer sheath (210).

D. Exemplary Handle Assembly and User Input Features

As shown in FIG. 1, handle assembly (100) includes a casing (110) having a lower portion that defines an obliquely oriented pistol grip (112) and an upper portion that supports a user interface feature (114) and releasably receives a battery pack (120), as described in greater detail below. Handle assembly (100) further includes several features that are operable to actuate anvil (400) and stapling head assembly (300). In particular, handle assembly (100) includes a rotatable knob (130), a safety trigger (140), a firing trigger (150), a motor (160), and a motor activation module (180). Knob (130) is coupled with trocar actuation rod (220) via a nut (not shown), such that coarse helical threading (224) will selectively engage a thread engagement feature within the interior of the nut; and such that fine helical threading (226) will selectively engage a thread engagement feature within the interior of knob (130). These complementary structures are configured such that trocar actuation rod (220) will first translate proximally at a relatively slow rate, and then translate proximally at a relatively fast rate, in response to rotation of knob (130).

It should be understood that when anvil (400) is coupled with trocar (330), rotation of knob (130) will provide corresponding translation of anvil (400) relative to stapling head assembly (300). It should also be understood that knob (130) may be rotated in a first angular direction (e.g., clockwise) to retract anvil (400) proximally toward stapling head assembly (300); and in a second angular direction (e.g., counterclockwise) to extend anvil (400) distally away from stapling head assembly (300). Knob (130) may thus be used to adjust a gap distance (d) between opposing stapling surfaces (412, 322) of anvil (400) and stapling head assembly (300) until a suitable gap distance (d) has been achieved, for example as shown in FIG. 7C described below.

Firing trigger (150) is operable to activate motor (160) to thereby actuate stapling head assembly (300) to staple and cut tissue clamped between anvil (400) and stapling head assembly (300). Safety trigger (140) is operable to selectively block actuation of firing trigger (150) based on the longitudinal position of anvil (400) in relation to stapling head assembly (300). Handle assembly (100) also includes components that are operable to selectively lock out both triggers (140, 150) based on the position of anvil (400) relative to stapling head assembly (300). For instance, safety trigger (140) may be blocked from rotating from an engaged position to a disengaged position until the position of anvil (400) relative to stapling head assembly (300) is within a predefined range. Accordingly, until the anvil position is within the predefined range, actuation of firing trigger (150) is blocked by safety trigger (140), thereby inhibiting firing of stapling head assembly (300).

Firing trigger (150) is operable to actuate a switch of motor activation module (180) (FIG. 1) when firing trigger (150) is pivoted proximally to a fired position. Motor activation module (180) is in communication with battery pack (120) and motor (160), such that motor activation module (180) is configured to provide activation of motor (160) with electrical power from battery pack (120) in response to firing trigger (150) actuating the switch of motor activation module (180). Thus, motor (160) will be activated when firing trigger (150) is pivoted. This activation of motor (160) will actuate stapling head assembly (300) via drive bracket (250), as described in greater detail below.

E. Exemplary Anastomosis Procedure with Circular Stapling Instrument

FIGS. 7A-7E show instrument (10) being used to form an anastomosis (70) between two tubular anatomical structures (20, 40). By way of example only, the tubular anatomical structures (20, 40) may comprise sections of a patient's esophagus, colon, or other portions of the patient's digestive tract, or any other tubular anatomical structures.

Figure 7A:
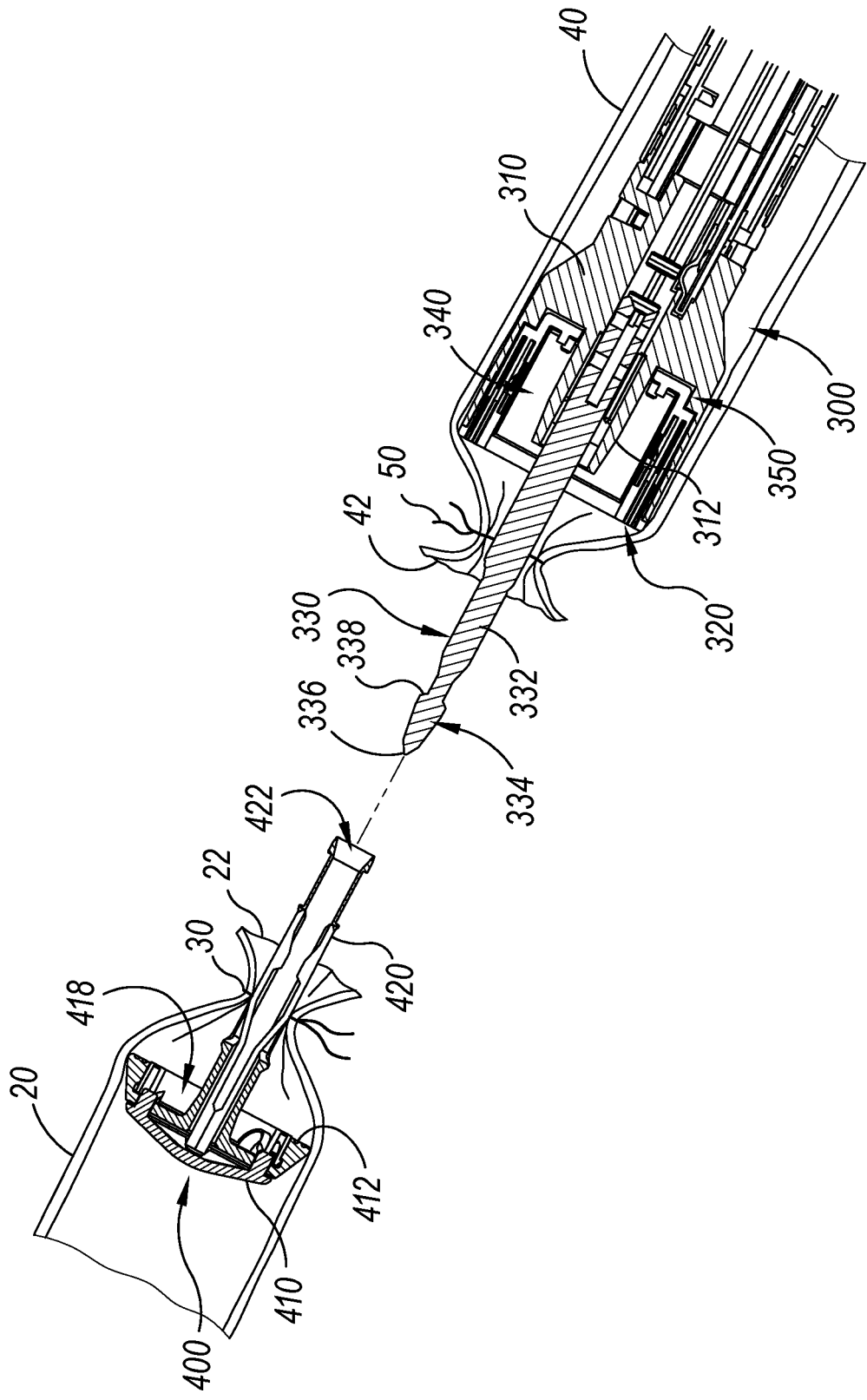
FIG. 7A depicts a cross-sectional side view of the anvil of FIG. 3 positioned within a first section of a digestive tract and the stapling head assembly of FIG. 4 positioned within a separate second section of the digestive tract, with the anvil separated from the stapling head assembly.

As shown in FIG. 7A, anvil (400) is positioned in one tubular anatomical structure (20) and stapling head assembly (300) is positioned in another tubular anatomical structure (40). As shown in FIG. 7A, anvil (400) is positioned in tubular anatomical structure (20) such that shank (420) protrudes from the open severed end (22) of tubular anatomical structure (20). In the present example, purse-string suture (30) is provided about a mid-region of shank (420) to generally secure the position of anvil (400) in tubular anatomical structure (20). Stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40). Stapling head assembly (300) is then urged distally to ensure that stapling head assembly (300) is fully seated at the distal end of tubular anatomical structure (40).

Figure 7B:
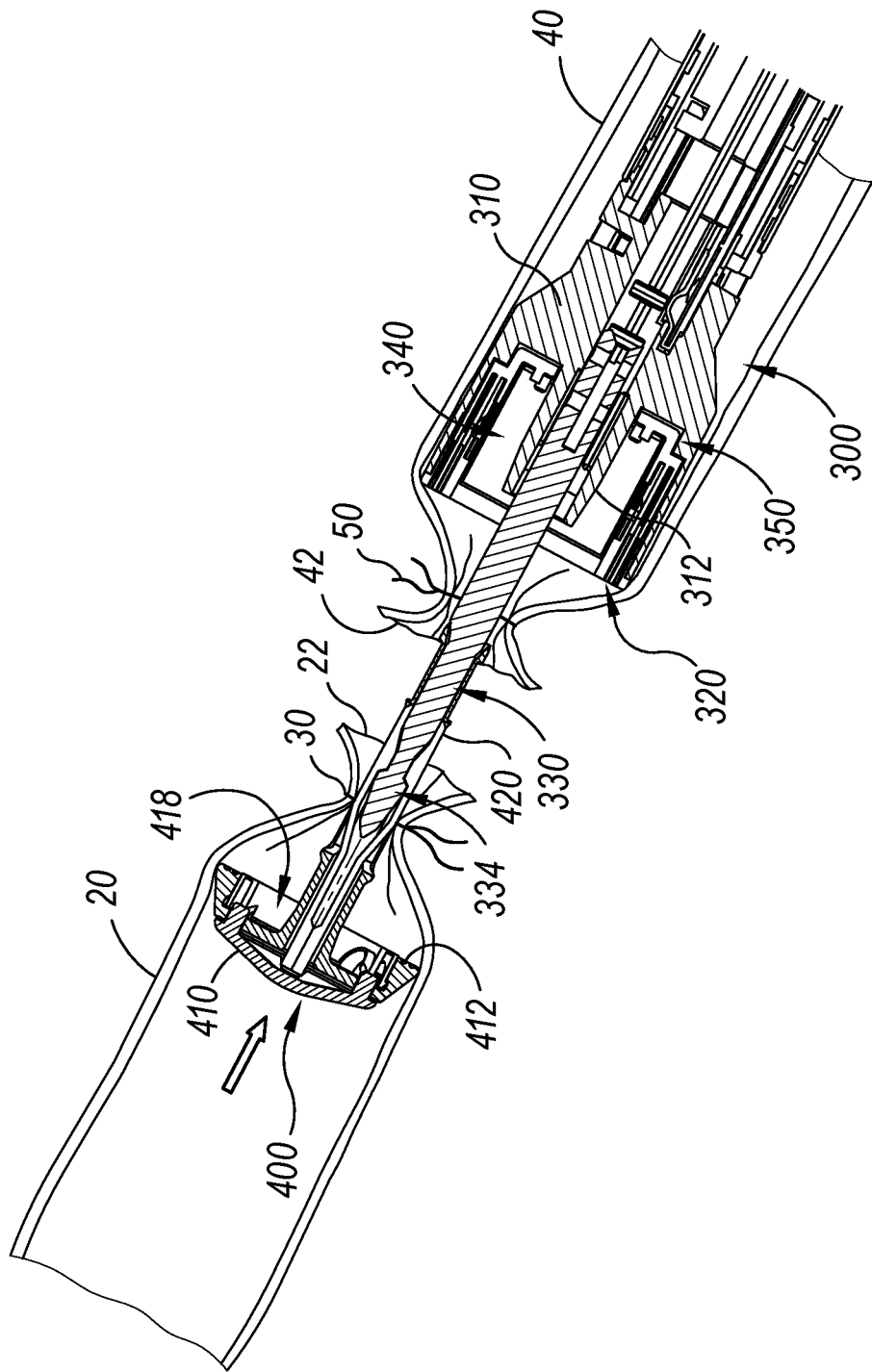
FIG. 7B depicts a cross-sectional side view of the anvil of FIG. 3 positioned within the first section of the digestive tract and the stapling head assembly of FIG. 4 positioned within the separate second section of the digestive tract, with the anvil secured to the stapling head assembly.
Figure 7C:
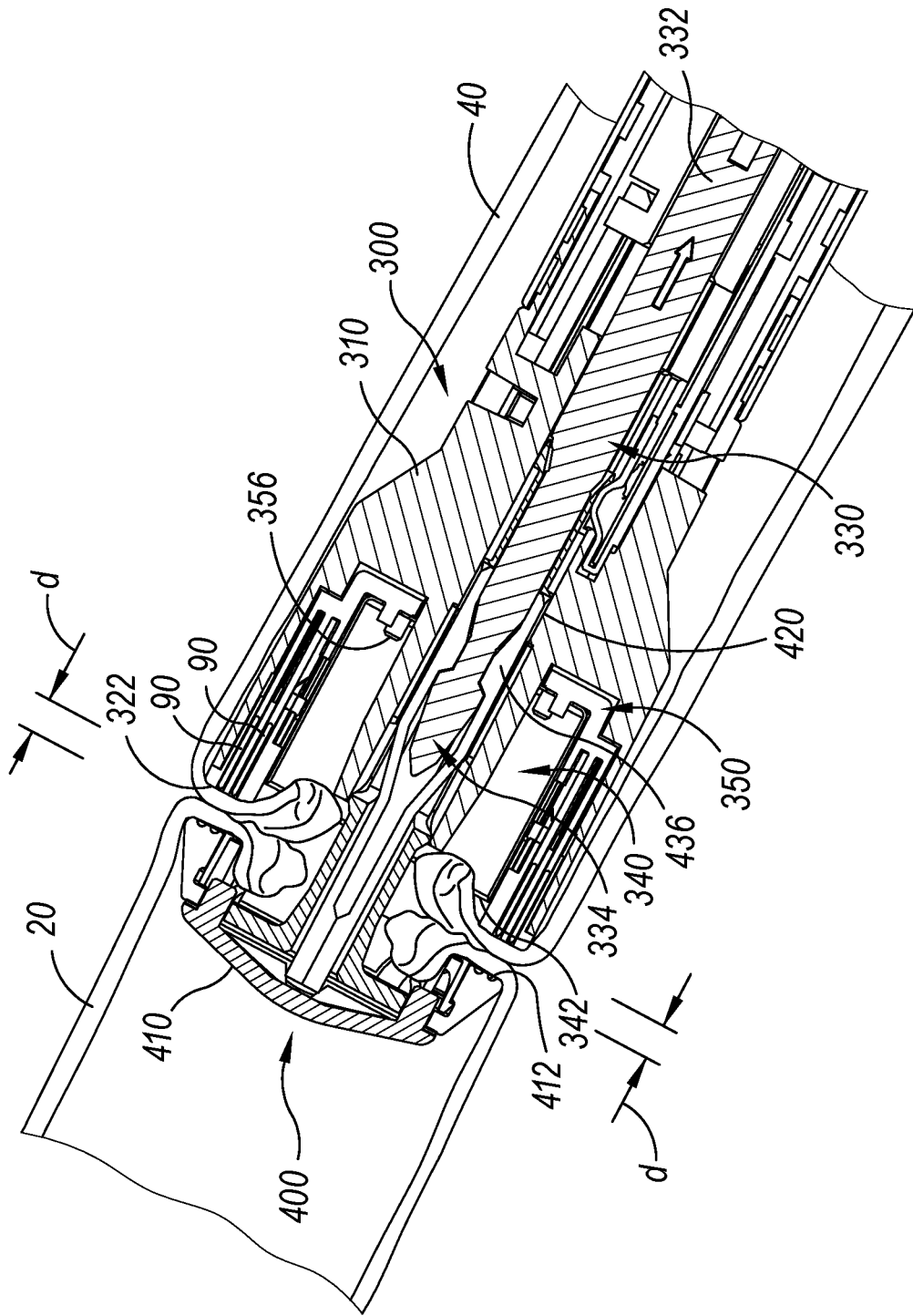
FIG. 7C depicts a cross-sectional side view of the anvil of FIG. 3 positioned within the first section of the digestive tract and the stapling head assembly of FIG. 4 positioned within the separate second section of the digestive tract, with the anvil retracted toward the stapling head assembly to thereby clamp tissue between the anvil and the stapling head assembly.

Next, anvil (400) is secured to trocar (330) by inserting trocar (330) into bore (422) as shown in FIG. 7B. Latch members (430) of anvil (400) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally. As shown in FIG. 7C, this proximal retraction of trocar (330) and anvil (400) compresses the tissue of tubular anatomical structures (20, 40) between surfaces (412, 322) of anvil (400) and stapling head assembly (300). As this occurs, the operator may observe the tactile resistance or feedback via knob (130) while turning knob (130), with such tactile resistance or feedback indicating that the tissue is being compressed. As the tissue is being compressed, the operator may visually observe the position of an indicator needle (not shown) within user interface feature (114) of handle assembly (100) to determine whether the gap distance (d) between opposing surfaces (412, 322) of anvil (400) and stapling head assembly (300) is appropriate; and make any necessary adjustments via knob (130).

Once the operator has appropriately set the gap distance (d) via knob (130), the operator pivots safety trigger (140) toward pistol grip (112) to enable actuation of firing trigger (150). The operator then pivots firing trigger (150) toward pistol grip (112), thus causing firing trigger (150) to actuate the switch of motor activation module (180) and thereby activate motor (160) to rotate. This rotation of motor (160) causes actuation (or "firing") of stapling head assembly (300) by actuating drive bracket (250) distally to thereby drive knife member (340) and staple driver member (350) distally together, as shown in FIG. 7D.

As knife member (340) translates distally, cutting edge (342) of knife member (340) cuts excess tissue that is positioned within annular recess (418) of anvil (400) and the interior of knife member (340). Additionally, washer (417) positioned within annular recess (418) of anvil (400) is broken by knife member (340) when the knife member (340) completes a full distal range of motion from the position shown in FIG. 7C to the position shown in FIG. 7D. It should be understood that washer (417) may also serve as a cutting board for knife member (340) to assist in cutting of tissue.

Figure 7D:
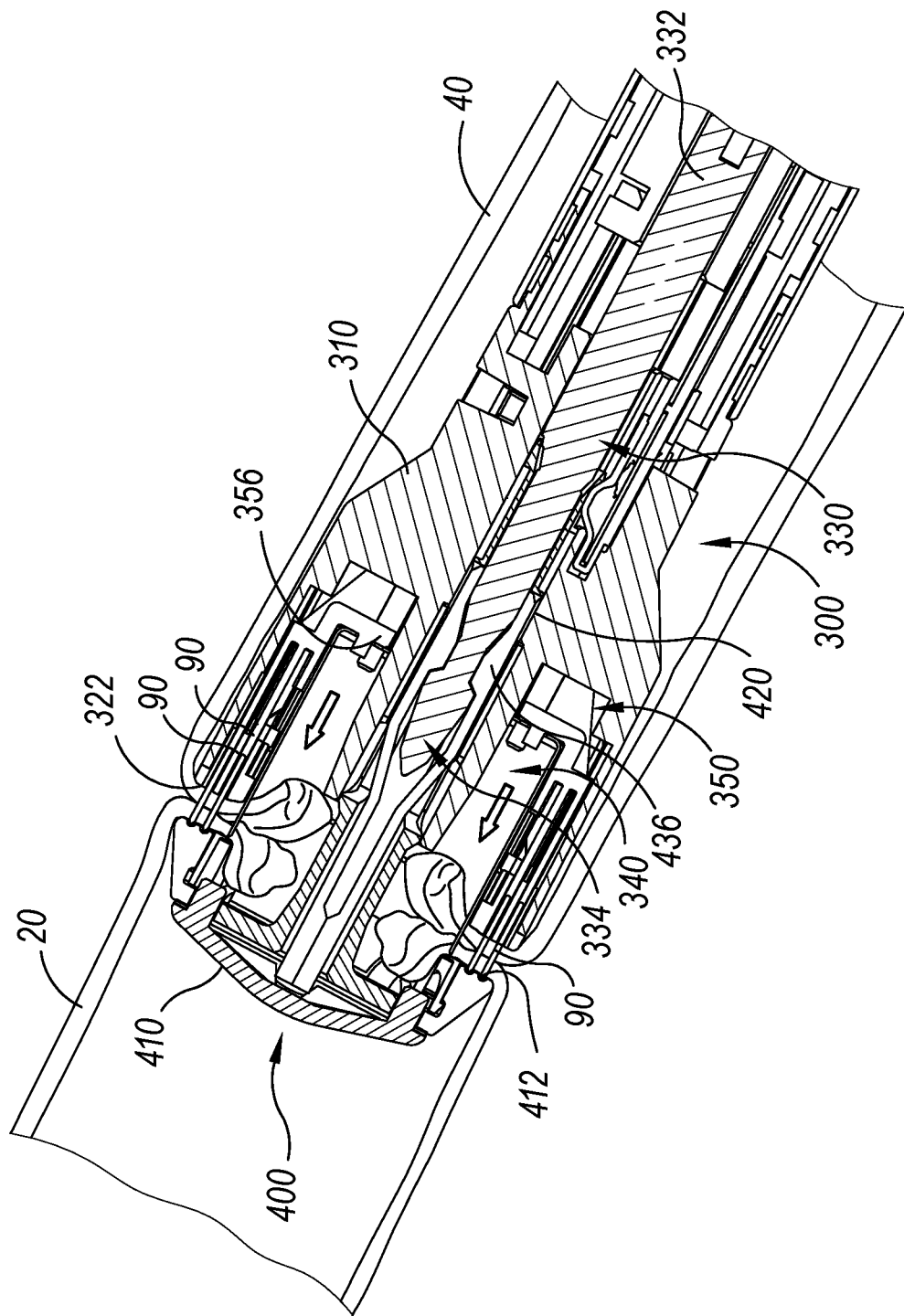
FIG. 7D depicts a cross-sectional side view of the anvil of FIG. 3 positioned within the first section of the digestive tract and the stapling head assembly of FIG. 4 positioned within the second section of the digestive tract, with the stapling head assembly actuated to sever and staple the clamped tissue and thereby joining the first and second sections of the digestive tract.

As staple driver member (350) translates distally from the position shown in FIG. 7C to the position shown in FIG. 7D, staple driver member (350) drives staples (90) through the tissue of tubular anatomical structures (20, 40) and into staple forming pockets (414) of anvil (400). Staple forming pockets (414) deform the driven staples (90) into a "B" shape or a three-dimensional shape, for example, such that the formed staples (90) secure the ends of tissue together, thereby coupling tubular anatomical structure (20) with tubular anatomical structure (40).

Figure 7E:
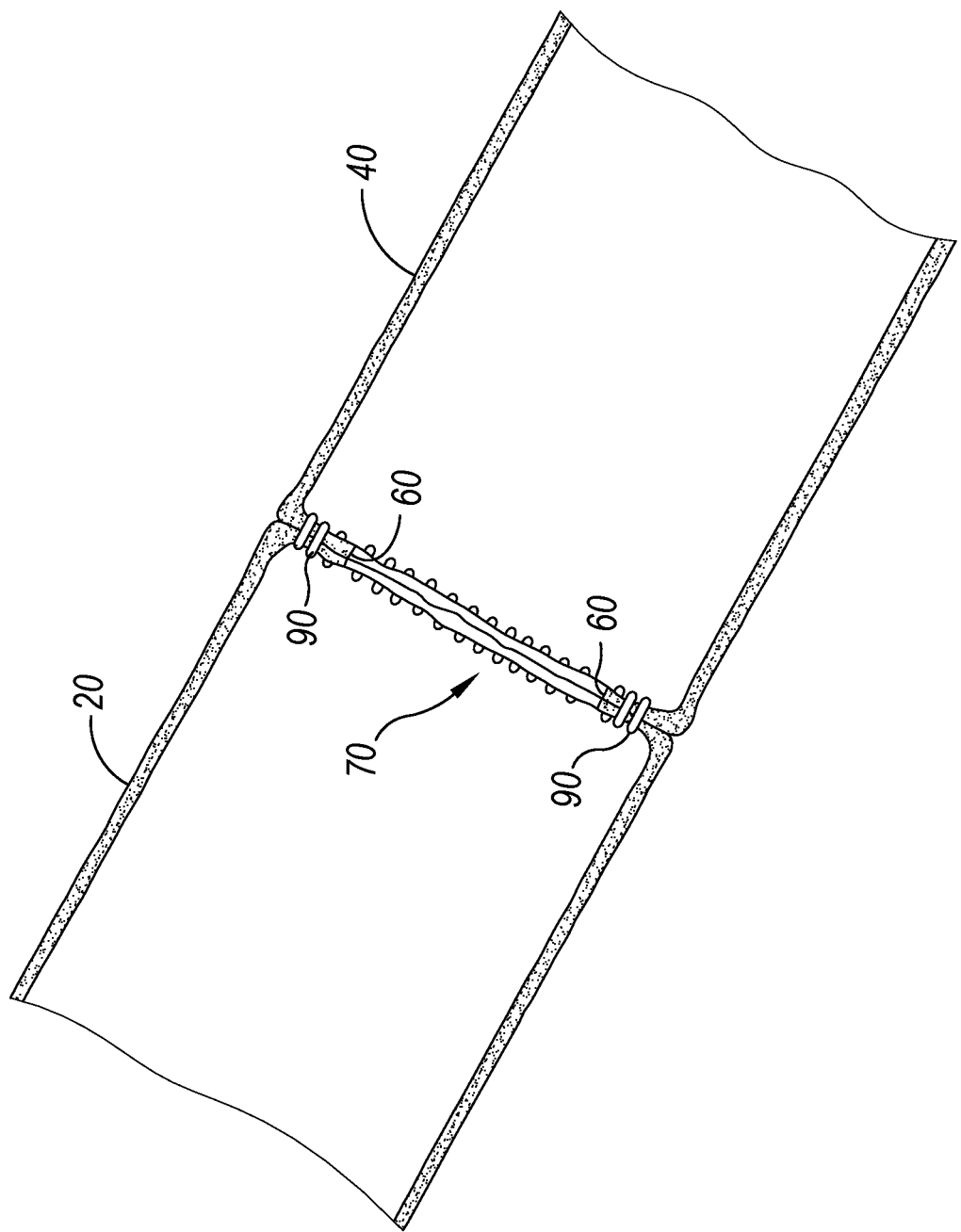
FIG. 7E depicts a cross-sectional side view of the first and second sections of the digestive tract of FIG. 7A joined together at an end-to-end anastomosis formed with the circular stapler of FIG. 1.

After the operator has actuated (or "fired") stapling head assembly (300) as shown in FIG. 7D, the operator rotates knob (130) to drive anvil (400) distally away from stapling head assembly (300), thereby increasing the gap distance (d) to facilitate release of the tissue between surfaces (412, 322). The operator then removes instrument (10) from the patient, with anvil (400) still secured to trocar (330). With instrument (10) removed, the tubular anatomical structures (20, 40) are left secured together by two annular arrays of staples (90) at an anastomosis (70) as shown in FIG. 7E. The inner diameter of the anastomosis (70) is defined by the severed edge (60) left by knife member (340).

II. Exemplary Staple Driver Member with Independently Actuating Staple Drivers

As mentioned above, staple driver member (350) includes two concentric annular arrays of staple drivers (352). As best shown in FIG. 5, each staple driver (352) is fixed relative to the rest of staple driver member (350), which includes all other staple drivers (352). As also mentioned above, each staple opening (324) is configured to slidably receive and provide a pathway for a corresponding staple driver (352) to drive a corresponding staple distally through deck member (320) and into a corresponding staple forming pocket (414)

when stapling head assembly (300) is actuated. Therefore, during the initial assembly of stapling head assembly (300), the concentric arrays of staple drivers (352) are inserted together into respective staple openings (324) of the annular array of staple openings (324).

Because staple driver member (350) has staple drivers (352) that are fixed relative to each other, the tolerance stack (i.e., the sum total of individual feature tolerances) during the manufacturing process of staple driver member (350) and annular deck member (320) may accumulate past a predetermined acceptable tolerance range. If the tolerance stack of staple drivers (352) accumulates past the predetermined acceptable tolerance range, individual staple drivers (352) may fail to suitably fit within their corresponding staple openings (324) during the assembly process. In other words, during the manufacturing process, where each staple driver (352) is fixed relative to each other, the chances may be relatively high that one or more staples drivers (352) are formed with a deviation from their intended location relative to each other. If this deviation is too great, one or more staple drivers (352) may not suitably align to slidingly engage a respective opening (324) during assembly, thereby resulting in excessive friction (and resultant input force required for firing), or complete blocking of relative movement, between the manufactured staple driver member (350) and staple deck member (320), thus rendering these components unusable with one another.

To accommodate this accumulated tolerance stack, staple openings (324) defined by staple deck member (320) could be made larger Additionally, or alternatively, staple drivers (352) could be made smaller. However, these modifications to accommodate an undesirable tolerance stack may ultimately leave a less than desirable fit with excessive "play" between staple drivers (352) and respective openings (324), which could result in one or more unformed staples (90) becoming misaligned with their respective staple forming pockets (414) of anvil (400) during firing such that staples (90) are left malformed and ineffective to properly seal tissue. To avoid this scenario, a tighter fit between staple drivers (352) and respective staple openings (324) may be desirable, as tighter fit between staple drivers (352) and respective staple openings (324) may promote proper alignment of unformed staples (90) with their respective staple forming pockets (414) and lead to more accurate formation of staples (90) against staple forming pockets (414). Therefore, rather than having staple drivers (352) integrally formed with one another from a single piece of material or formed in such a way as to be fixed relative to each other, it may be desirable to form staple drivers (352) into independently actuatable segments (each capable of firing a single staple, two staples, or any other suitable amount of staples) that may be individually inserted into their respective staple openings (324) and then fired by a separated portion of staple driver member (350).

Figure 8:
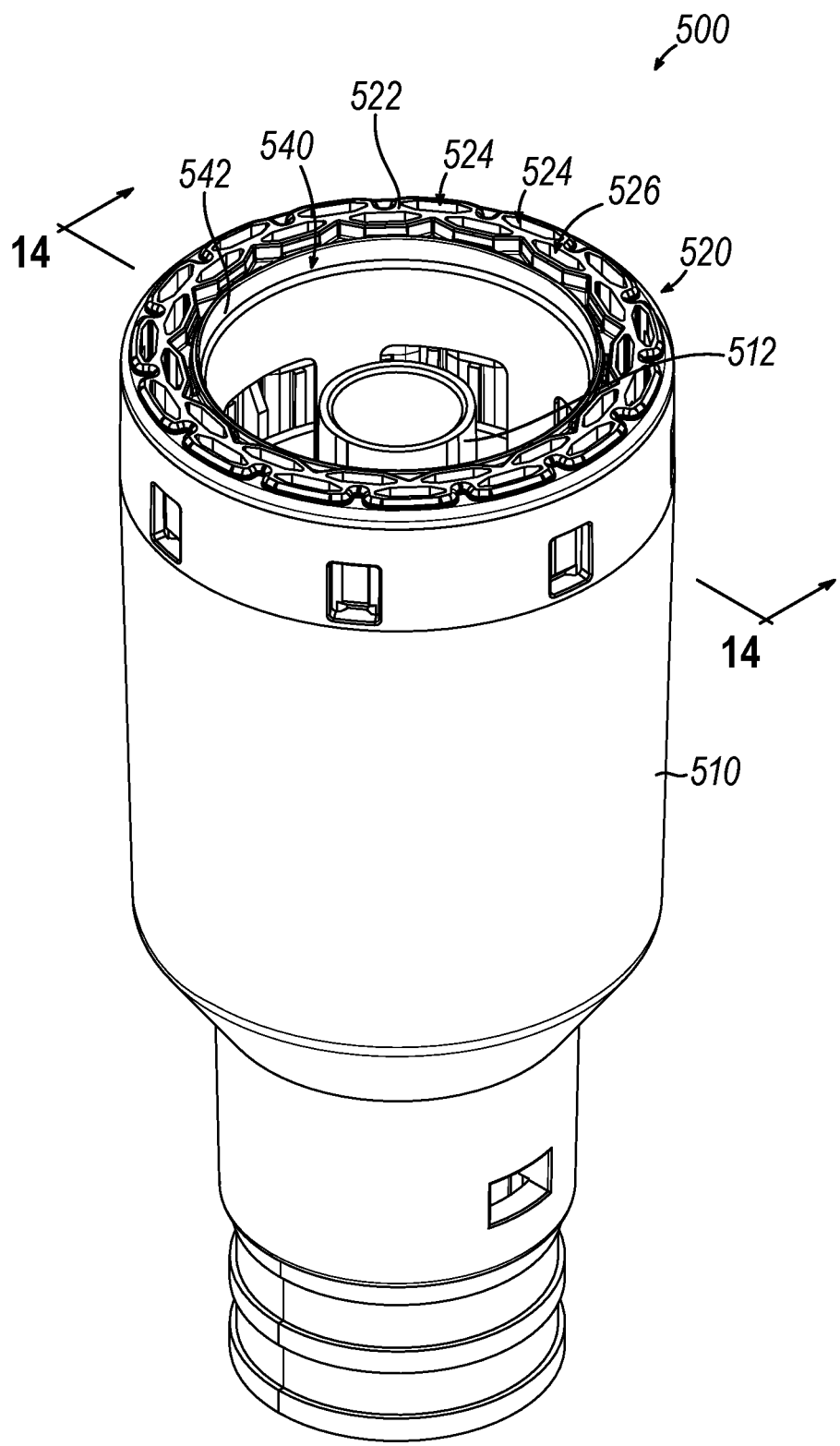
FIG. 8 depicts a perspective view of an alternative stapling head assembly that may be readily incorporated into the circular surgical stapler of FIG. 1.

FIGS. 8-9 show an alternative stapling head assembly (500) that may be readily incorporated into circular surgical stapling instrument (10) described above. Therefore, stapling head assembly (500) may be substantially similar to stapling head assembly (300) described above, with differences elaborated herein. In particular, stapling head assembly (500) includes a plurality of staple driving bodies (560, 570) that may be inserted individually into a respective staple opening (524); which may reduce an accumulated tolerance stack as described above, thereby allowing a tighter fit between staple openings (524) and a respective staple driving body (560, 570).

Turning to FIG. 9, stapling head assembly (500) includes a tubular body member (510), an inner core member (512), an annular deck member (520), a deck surface (522) defining a plurality of staple openings (524), a trocar (not shown), a cylindraceous knife member (540), a sharp circular cutting edge (542), and a staple driver assembly (550); which may be substantially similar to tubular body member (310), inner core member (312), annular deck member (320), deck surface (322), staple openings (324), trocar (330), cylindraceous knife member (340), cutting edge (342), and staple driver member (350), described above, respectively, with differences elaborated below.

Similar to staple driver member (350) described above, staple driver assembly (550) is configured to actuate relative to tubular body member (510) in order to drive a plurality of staples through staple openings (524) and against anvil (400). However, rather than having staple drivers (352) that are fixed relative to the rest of staple driver assembly (550), staple driver assembly (550) includes a proximal driver body (552), an inner circumferential array of driving bodies (568), and an outer circumferential array of driving bodies (578). Inner circumferential array of driving bodies (568) is formed from a plurality of individual inner staple driving bodies (560). Similarly, outer circumferential array of driving bodies (578) is formed from a plurality of individual outer staple driving bodies (570). Individual segmented driving bodies (560, 570) may be individually inserted into a respective staple opening (524). While in the current example, each driving body (560, 570) is separated from each other into individual segments, in some instances, driving bodies (560, 570) may be fixed to one or more other driving bodies (560, 570) such that one individual segment may be configured to drive more than one staple.

Proximal driver body (552) includes an outer array of pushing bodies (554) and an inner array of pushing bodies (556). Similar to staple driver member (350) of stapling head assembly (300) described above, proximal driver body (552) is fixedly secured to a distal end of stapling head assembly driver (240) (see FIG. 6) such that proximal driver body (552) is configured to translate relative to tubular body member (510) and annular deck member (520) in response to translation of stapling head assembly driver (240) relative to outer sheath (210). Each pushing body of outer array of pushing bodies (554) is configured to align with and engage a respective outer staple driving body (570), while inner array of pushing bodies (556) are configured to align with and engage a respective inner staple driving body (560). As will be described in greater detail below, driving bodies (570, 560) may be inserted into respective stapling openings (524A, 524B) (see FIGS. 12-13) without pushing bodies (554, 556) being fixed to a respective staple driving body (570, 560).

Figure 10:
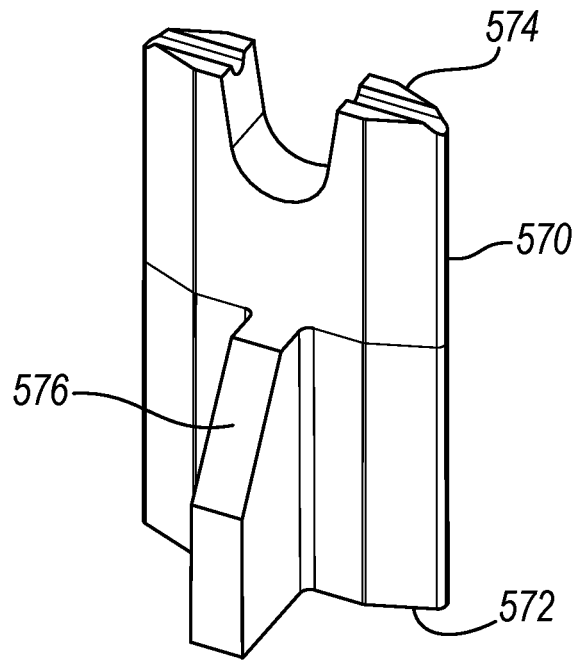
FIG. 10 depicts a perspective view of an outer staple driving body.
Figure 11:
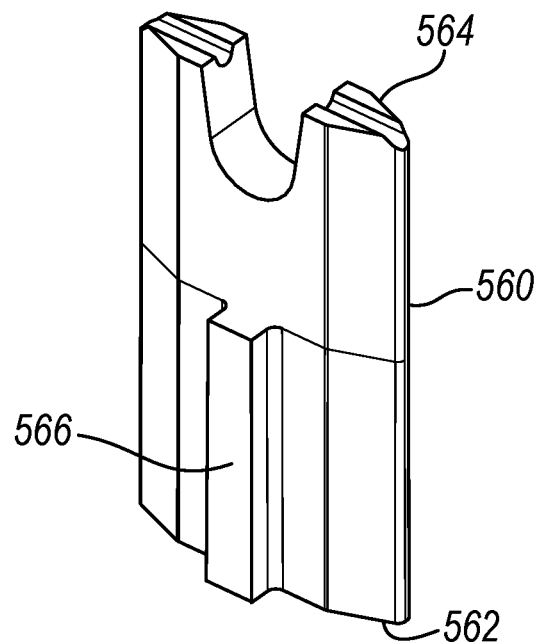
FIG. 11 depicts a perspective view of an inner staple driving body.

As best shown in FIGS. 10-11, each inner staple driving body (560) and outer staple driving body (570) includes a proximal surface (562, 572), a distal staple engagement surface (564, 574), and a stop body (566, 576). Inner staple driving bodies (560) are dimensioned to slidingly fit within a respective staple opening (524B) while outer staple driving bodies (570) are dimensioned to slidingly fit within a respective staple opening (524A).

Proximal surfaces (562, 572) are dimensioned to engage respective pushing bodies (556, 554) such that when assembled, distal actuation of proximal driver body (552) also leads to distal actuation of staple driving bodies (560, 570). When assembled, staple driving bodies (560, 570) may extend proximally such that proximal surfaces (562, 572) and pushing bodies (556, 554) are proximal relative to a proximal end of staple openings (524B,524A) (see FIGS. 14A-14B). Since proximal surfaces (562, 572) extend proximal relative to proximal end of staple opening (524B, 524A), pushing bodies (556, 554) are also proximal relative to staple openings (524B, 524A). Therefore, pushing bodies (556, 554) do not need to slidingly fit within openings (524B, 524A) such that proximal driver body (552) may be manufactured without concern of slidingly fitting pushing bodies (556, 554) within respective staple openings (524B, 524A). Therefore, staple driving body (560, 570) and staple openings (524) may be manufactured with tighter tolerances while still maintaining a slidable relationship between driving body (560, 570) and a respective staple opening (524), thereby increasing the accuracy of fired staples.

Figure 14A:
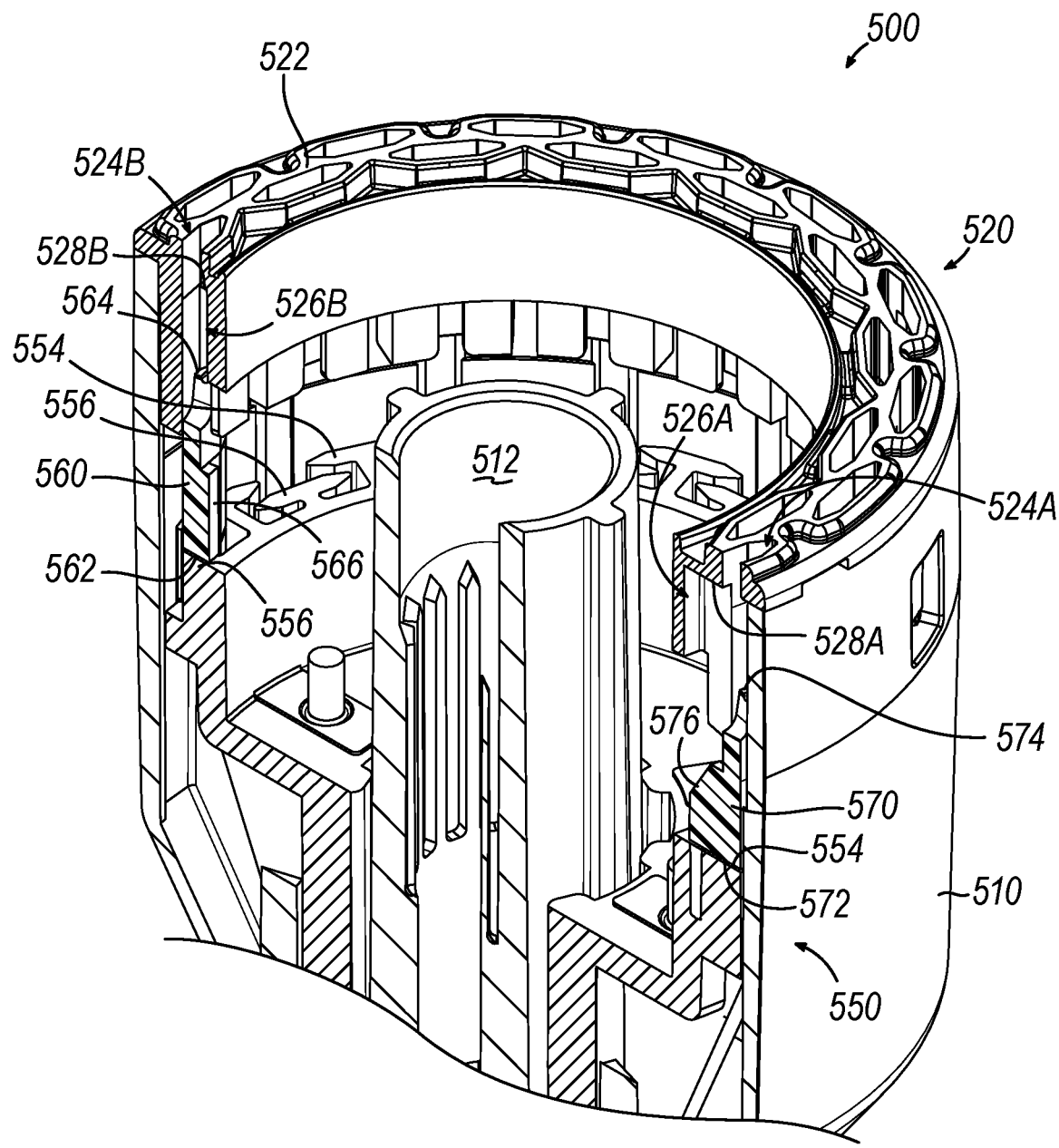
FIG. 14A depicts a sectional perspective view of the staple head assembly of FIG. 8 in a pre-fired position, taken along line 14-14 of FIG. 8.
Figure 14B:
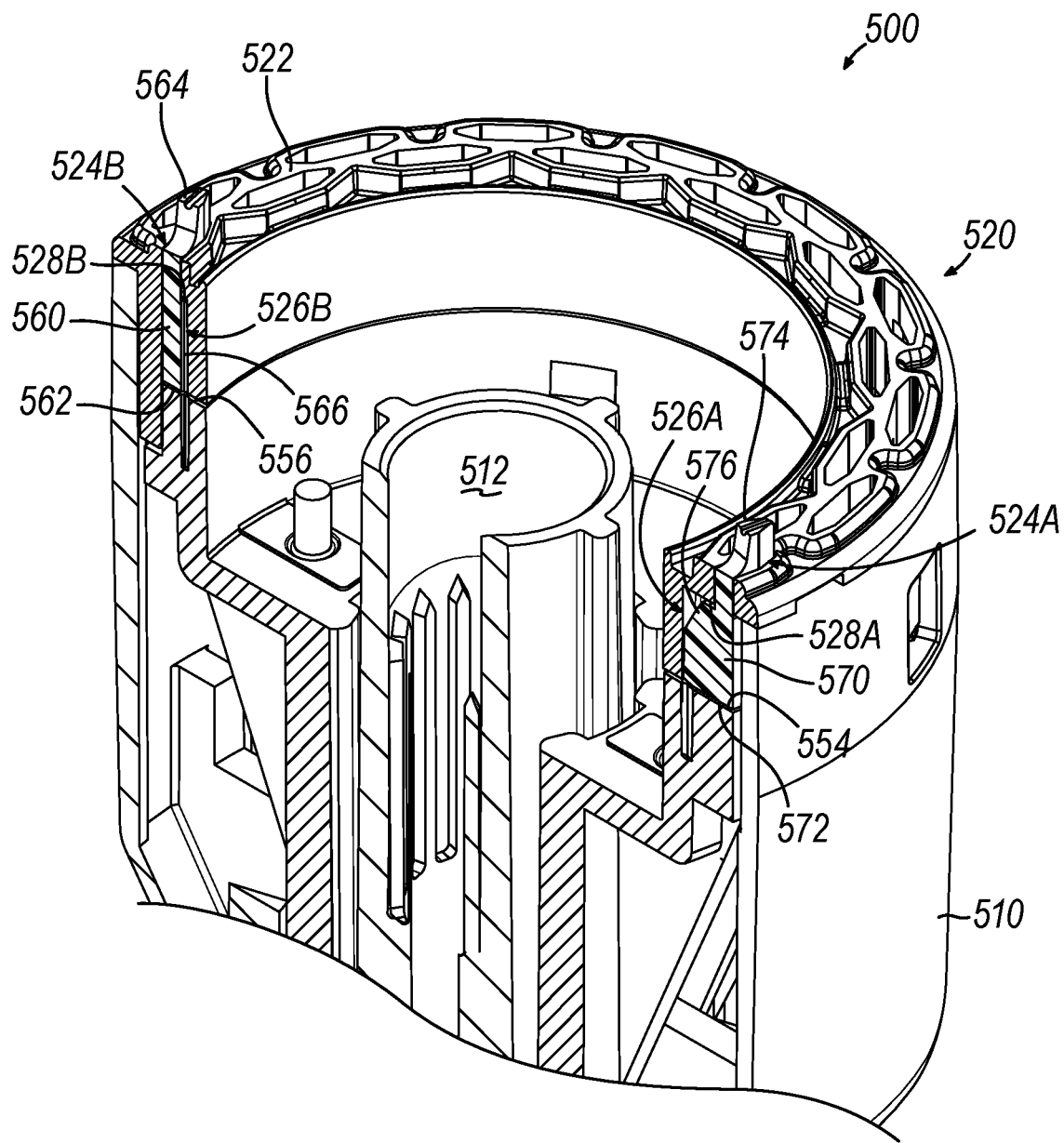
FIG. 14B depicts a sectional perspective view of the staple head assembly of FIG. 8 in a fired position, taken along line 14-14 of FIG. 8.

Distal staple engagement surfaces (564, 574) are configured to suitably engage a corresponding staple such that staple driving bodies (560, 570) may distally actuate (i.e., "fire") a staple against anvil (400) during the firing process as shown in FIG. 14A-14B. Distal staple engagement surfaces (564, 574) are dimensioned to slidingly fit within staple openings (524B, 524A) such that surfaces (564, 574) may suitably fire a staple against anvil (400) in accordance with the description herein. In some examples, as shown in FIG. 14B, staple engagement surfaces (564, 574) may be configured to extend distally past staple deck surface (522). Distal staple engagement surfaces (564, 574) may include any suitable features needed to engage and fire a staple in accordance with the description herein as would be apparent to one skilled in the art in view of the teachings herein.

Figure 12:
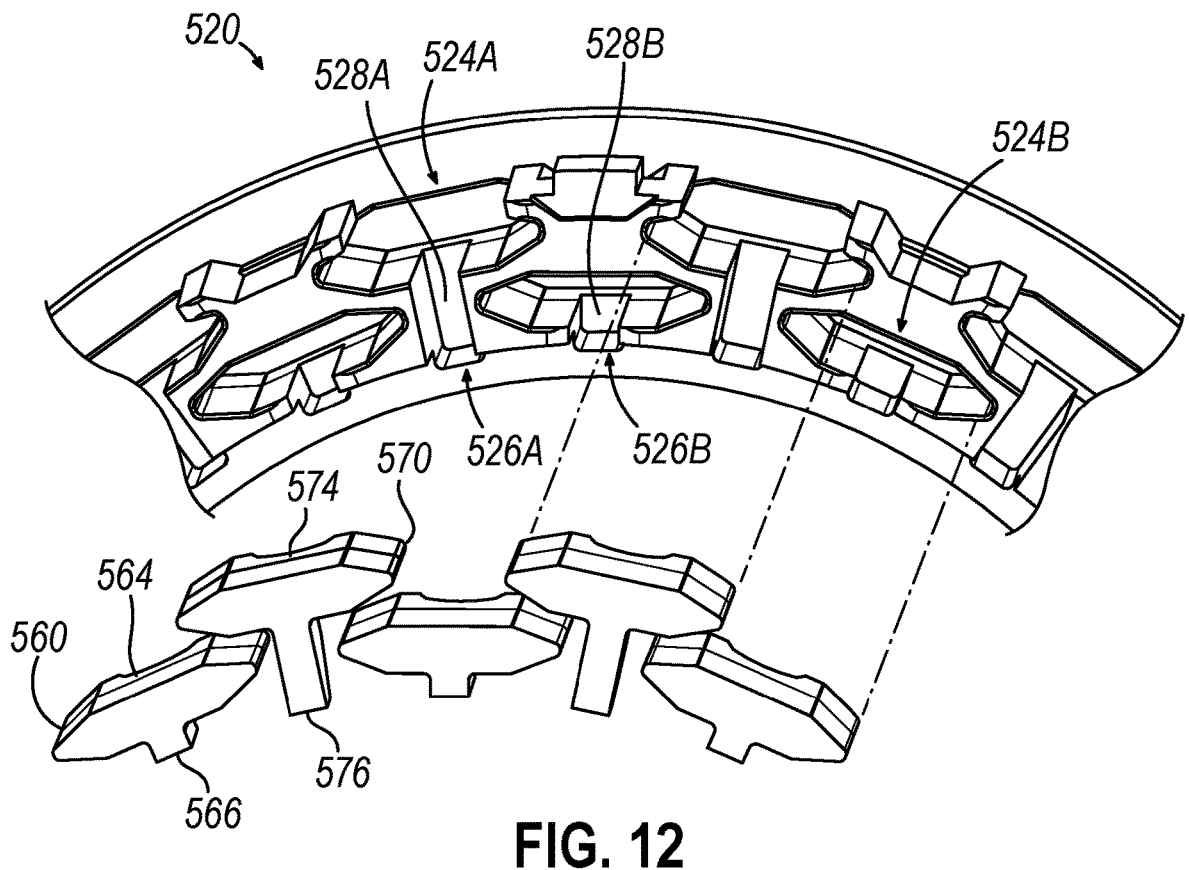
FIG. 12 depicts an enhanced exploded perspective view of an underside of a staple deck member of the staple head assembly of FIG. 8, a plurality of outer staple driving bodies of FIG. 10, and a plurality of inner staple driving bodies of FIG. 11.
Figure 13:
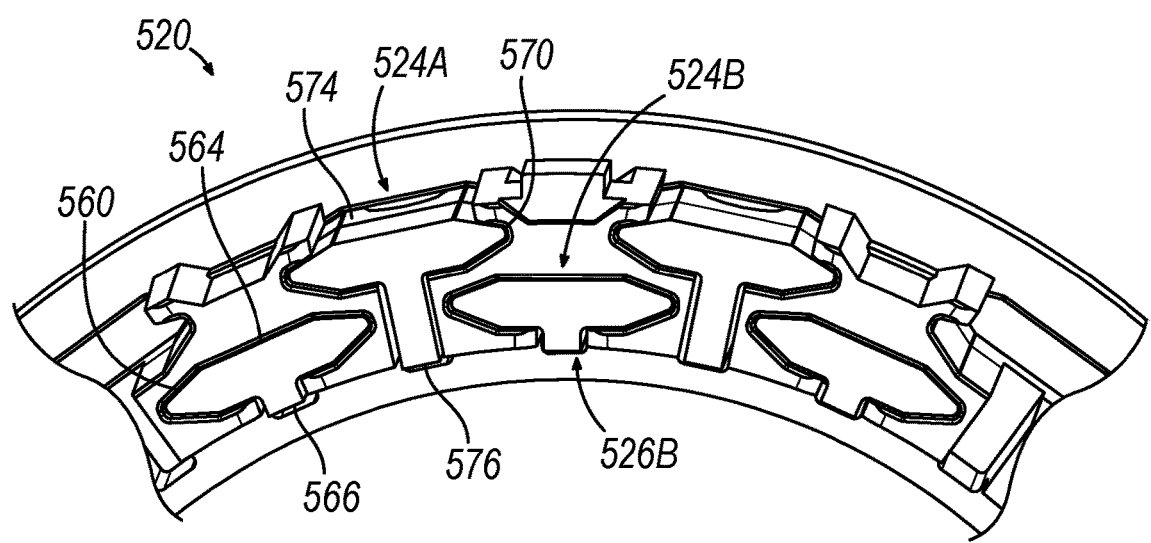
FIG. 13 depicts an enhanced exploded perspective view of an underside of a staple deck member of FIG. 12, a plurality of outer staple driving bodies of FIG. 10, and a plurality of inner staple driving bodies of FIG. 11.

During assembly, as shown between FIGS. 12-13, staple driving bodies (560, 570) may be individually inserted into a respective staple opening (524B, 524A). Since staple driving bodies (560, 570) may be inserted into respective staple openings (524B, 524A) in a segmented fashion (e.g., in the current example, one body (560, 570) at a time), an accumulated tolerance stack associated with bodies (560, 570) being fixed to every other body (560, 570) is reduced or eliminated. Therefore, as shown in FIG. 13, the fit between staple driving bodies (560, 570) and their respective staple opening (524,B 524A) may be tighter, closer, etc., as compared to if bodies (560, 570) were fixed relative to every other body (560, 570). Therefore, use of segmented bodies (560, 570) may lead to more accurately fired staples against staple forming pockets (414). While in the current example, individual staple driving bodies (560, 570) are associated with (A) a specific staple to be fired, and (B) a specific array (i.e. inner or outer array) of staple openings; this is merely optional. In some instances, staple driving bodies (560, 570) may be associated with multiple staples, with such staples ranging between inner and outer arrays of staples openings (524A, 524B). Any suitable arrangement of staple driving bodies related to corresponding staple opening (524A, 524B) may be utilized as would be apparent to one skilled in the art in view of the teachings herein.

Since staple driving bodies (560, 570) are not fixedly attach to proximal driver body (552), it may be desirable to have some sort of interaction between individual staple driving bodies (560, 570) and other components of stapling head assembly (500) to prevent staple driving bodies (560, 570) from falling out of openings (524B, 524A). Therefore, staple driving bodies (560, 570) may utilize a feature in order to prevent bodies (560, 570) from accidentally sliding out the distal end of staple openings (524B, 524A). In the current example, staple driving bodies (560, 570) include a respective stop body (566, 576) that are slidingly contained within a stop channel (526B, 526A). As best shown in FIGS. 12 and 14A-14B, stop channels (526B, 526A) terminate into a stop surface (528B, 528A). Stop surfaces (528B, 528A) may engage a respective stop body (560, 570) in order to prevent staple driving bodies (560, 570) from exiting a distal end of staple openings (524B, 524A). While in the current example, stop bodies (566, 576) and stop channel (526B, 226A) are used to inhibit staple driving bodies (560, 570) from falling out the distal end of staple openings (524B, 524A), any other suitable feature may be utilized as would be apparent to one skilled in the art in view of the teachings herein. For example, proximal surface (562, 572) may be dimensioned larger than proximal ends of staple openings (524B, 524A) such that a proximal portion of driving bodies (560, 570) abuts against an underside of staple deck member (520) defining proximal ends of staple openings (524B, 524A) in order to inhibit staple driving bodies (560, 570) from falling out the distal end of staple openings (524B, 524A).

FIGS. 14A-14B show an exemplary actuation of staple driver assembly (550). It should be understood that actuation of staple driver assembly (550) may be utilized in order to fire staples housed within staple openings (524A, 524B) against staple forming pockets (414) of anvil (400) while anvil (400) and deck surface (522) define a suitable gap distance and grasp tissue. As shown between FIGS. 14A-14B, proximal driver body (552) may be actuated distally such that pushing bodies (554, 556) actuate staple engagement surfaces (574, 564) of driving bodies (570, 560) distally past deck surface (522). Distal actuation of staple driving bodies (570, 560) actuates staples (which may be suitably engaged with staple engagement surfaces (574, 564)) out of staple openings (524A, 524B) and against respective staple forming pockets (414) of anvil (400). As best shown in FIG. 14B, in some instances during firing of driving bodies (560, 570), stop bodies (566, 576) may make contact with stop surfaces (528B, 528A) in order to prevent driving bodies (560, 570) from disassociating with their respective staple opening (524B, 524A). Once staples are suitably fired in accordance with the description herein, proximal driver body (552) may be actuated proximally, thereby allowing staple driving bodies (560, 570) to actuate back into their respective staple openings (524B, 524A) as shown in FIG. 14A.

In some instances, it may be desirable for staple driving bodies (560, 570) and annular deck member (520) to have a retention feature that helps maintain staple driving bodies (560, 570) at or near the distal-most position of the firing process (as exemplified in FIG. 14B). For instance, staple driving bodies (560, 570) maintaining a position at or near the distal-most position of the firing process after staples have been fired may allow staple driving bodies (560, 570) to help push tissue off desk surface (522) once anvil (400) releases tissue in accordance with the description herein.

Figure 15A:
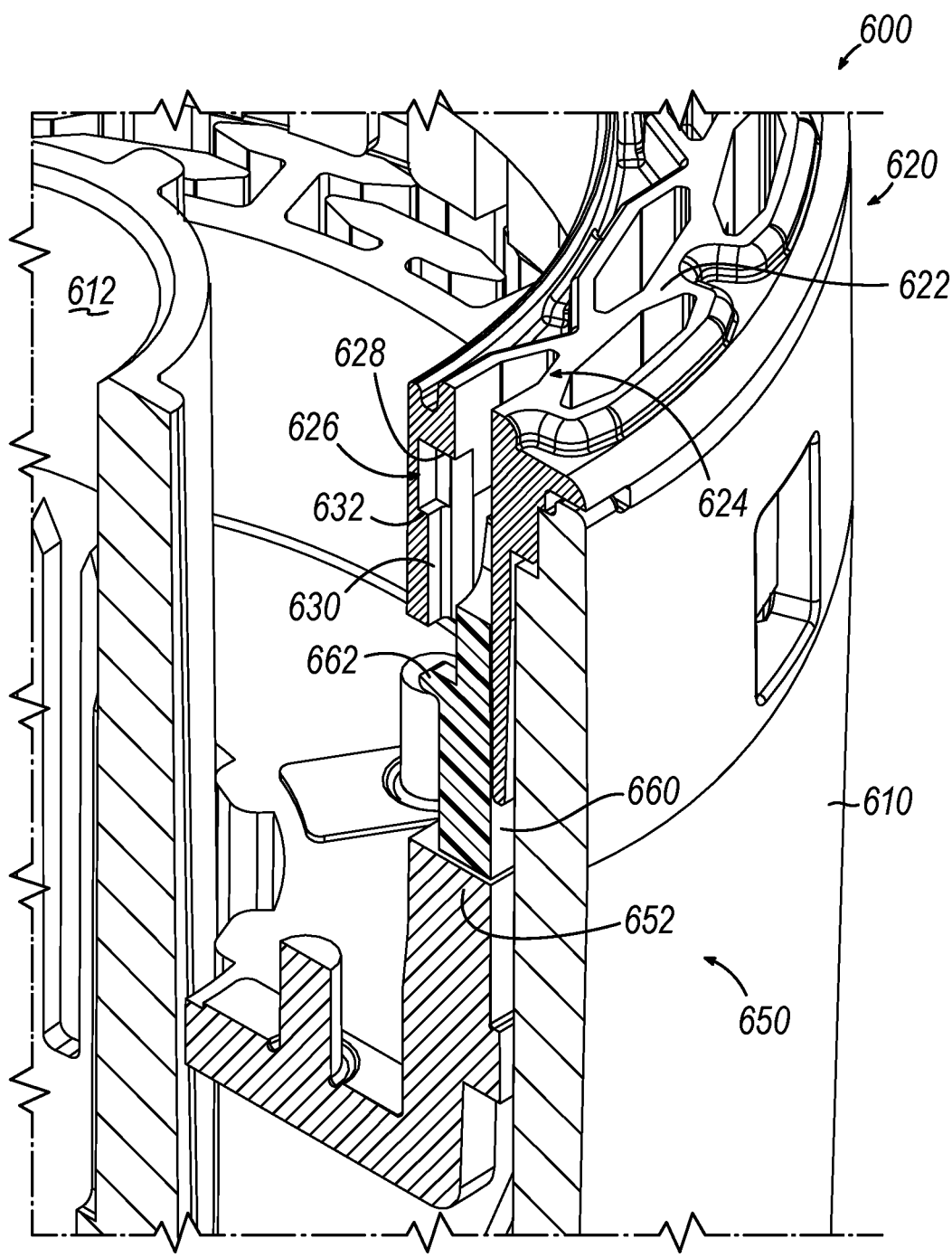
FIG. 15A depicts a sectional perspective view of an alternative staple head assembly in a pre-fired position, taken along a centerline thereof.
Figure 15B:
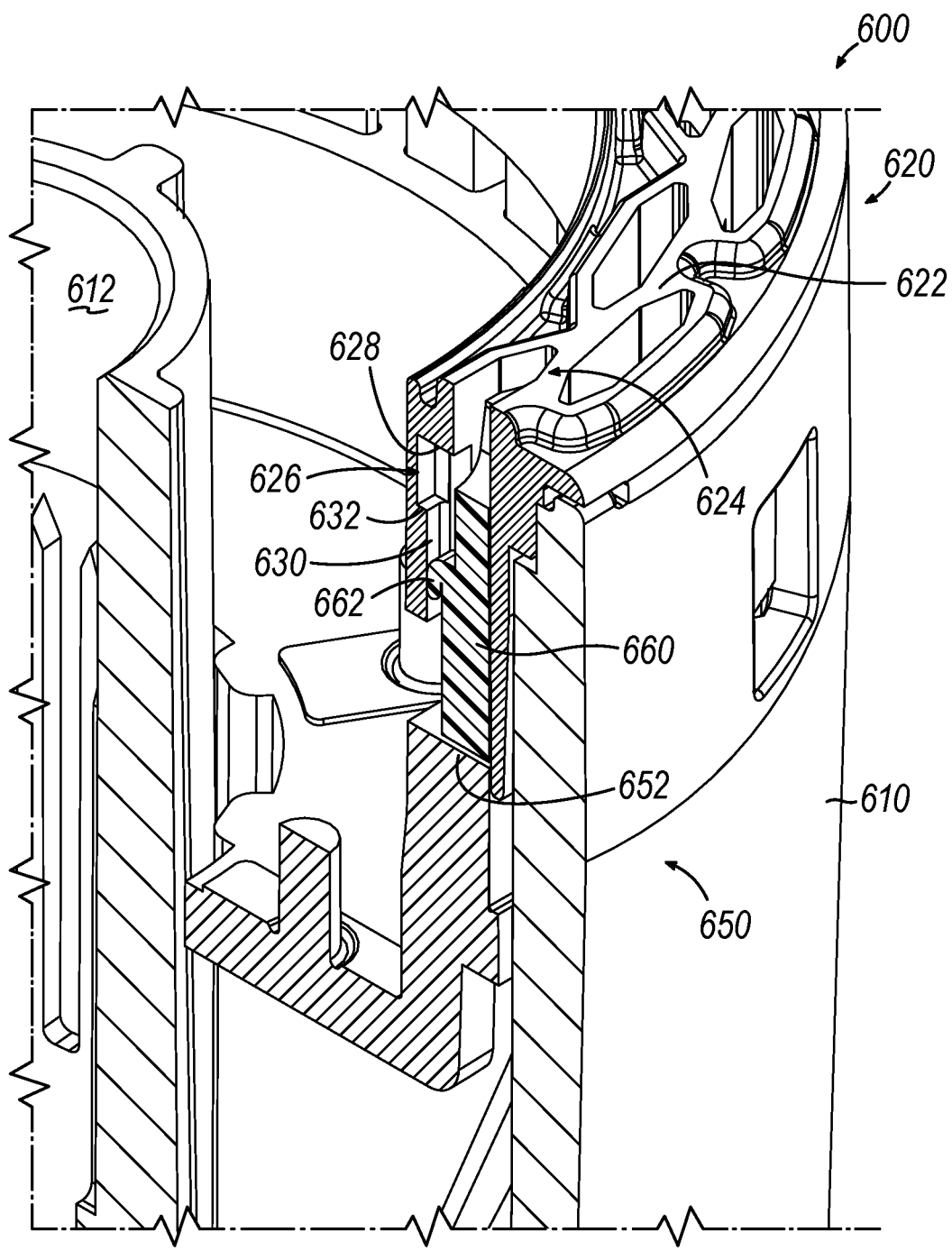
FIG. 15B depicts a sectional perspective view of the staple head assembly of FIG. 15A, taken along a centerline thereof, where a staple driver assembly is initially advanced distally.
Figure 15C:
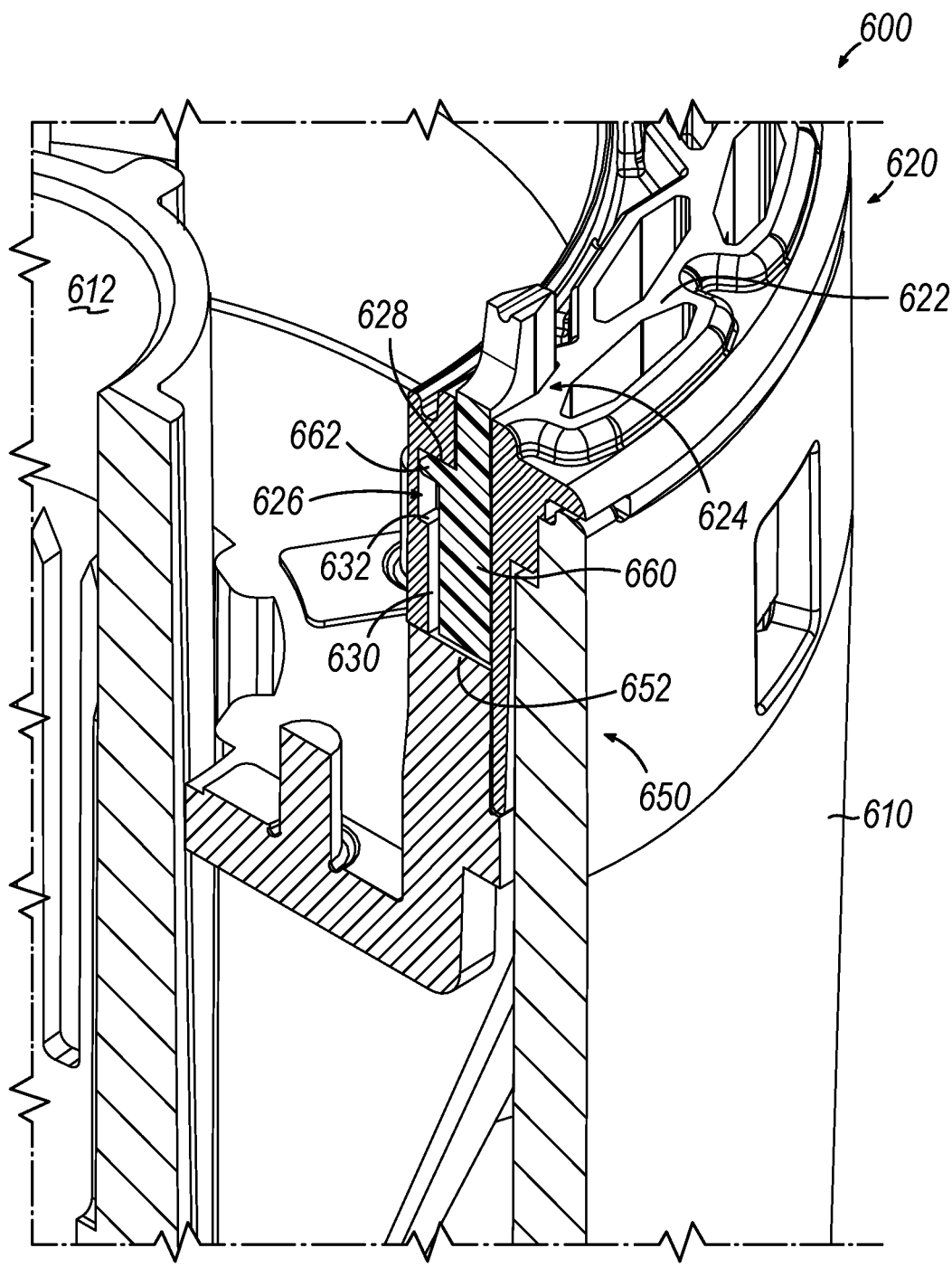
FIG. 15C depicts a sectional perspective view of the staple head assembly of FIG. 15A in a fired position, taken along a centerline thereof.

FIGS. 15A-15C show an exemplary alternative stapling head assembly (600) that may be readily incorporated into instrument (10) described above in replacement of stapling head assembly (300, 500) described above. Stapling head assembly (600) is substantially similar to stapling head assembly (500) described above with differences elaborated below. In particular, stapling head assembly (600) includes retention features configured to keep staple driving bodies (660) at or near the distal-most position such that a portion of staple driving bodies (660) extend distally past deck surface (622) (A) after the firing process, and (B) after proximal driver body (652) is proximally retracted.

Stapling head assembly (600) includes a tubular body member (610), an inner core member (612), an annular deck member (620) having a deck surface (622) defining a plurality of staple openings (624), a staple driver assembly (650), a proximal driver body (652), and a plurality of staple driving bodies (660); which are substantially similar to tubular body member (510), inner core member (512), annular deck member (520), deck surface (522), staple openings (524), staple driver assembly (550), proximal driver body (552), and staple driving bodies (560, 570) described above, respectively, with differences elaborated below. In particular, staple driving bodies (660) each include a resilient nub (662) while the portion of annular deck member (620) defining each stop channel (626) includes a stop surface (628), an interior surface (630), and a distally facing ledge (632). Stop channel (626) and stop surface (628) may function substantially similar to stop channel (526) and stop surface (528) described above. As will be described in greater detail below, resilient nub (662) is configured to engage ledge (632) after the firing process in order to keep staple driving body (660) at or near a distal-most position even after proximal driver body (652) is retracted proximally.

FIG. 15A-15D show an exemplary firing of staple driver assembly (650). It should be understood that actuation of staple driver assembly (650) may be utilized in order to fire staples housed within staple openings (624) against staple forming pockets (414) of anvil (400) while anvil (400) and deck surface (622) define a suitable gap distance and grasp tissue. As shown in FIGS. 15A-15B, resilient nub (662) is positioned along staple driving body (660) in order to abut against interior surface (630) of annular deck member (620) during the firing process. Resisting nub (662) is sufficiently resilient such that nub (662) may transition from a relaxed position to a flexed position due to contact with interior surface (630) while allowing proximal driver body (652) to distally actuate staple driving body (660) in order to fire a staple against staple forming pocket (414) of anvil (400). In other words, resilient nub (662) is configured to flex in response to contact with interior surface (630) during the firing process while accommodating distal translation of staple driving body (660) in order to fire staple in accordance with the description herein.

Figure 15D:
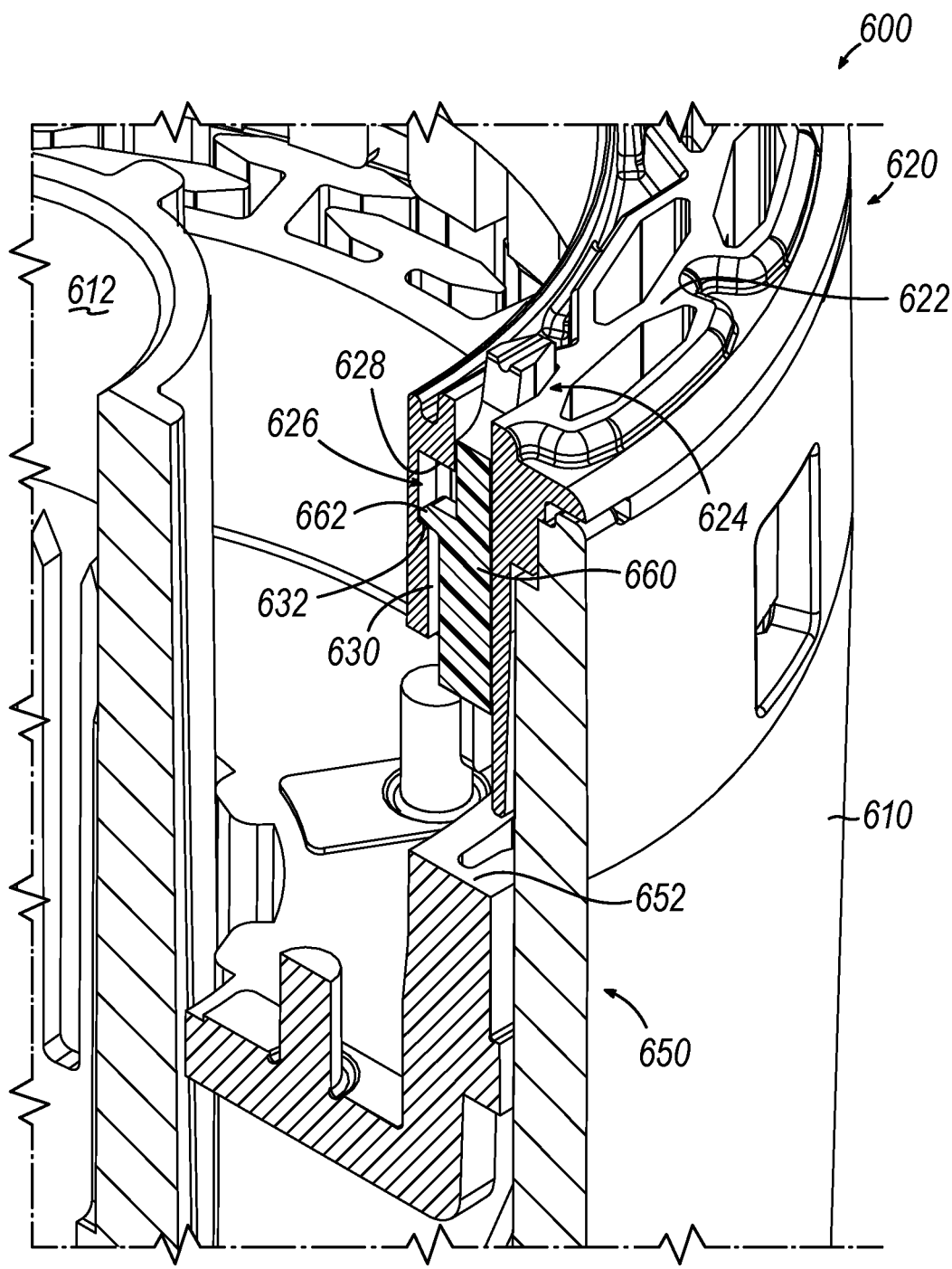
FIG. 15D depicts a sectional perspective view of the staple head assembly of FIG. 15A in a post-fired position, taken along a centerline thereof.

As shown between FIG. 15B-15C, once resilient nub (662) is actuated distally past interior surface (630), resilient nub (662) is sufficiently resilient to return to it relaxed position. As shown in FIG. 15C, resilient nub (662) (or another suitable portion driving body (660)) may also engage stop surface (628) to inhibit staple driving body (660) from actuating distally out of association with staple opening (624). Next, as shown in FIG. 15D, proximal driver body (652) may be retracted proximally. However, with resilient nub (662) in the relaxed position, nub (662) may engage ledge (632) of annular deck member (620). Engagement between ledge (632) and nub (662) may be sufficient to inhibit staple driving body (660) from completely proximally retracting back into staple opening (624), even after proximal driver body (652) is no longer in engagement with staple driving body (660). Allowing a portion of staple driving body (660) to extend distally past deck surface (622) after the firing process may help tissue captured between deck surface (622) and anvil (400) to disengage from deck surface (622) after the firing process, thereby acting as an anastomosis release feature. In other words, engagement between nub (662) and ledge (632) after the firing process may allow a distal portion of staple driving body (660) to push tissue once captured between deck surface (622) and anvil (400), off of deck surfaced (622) such that once anvil (400) is actuated distally after the firing process, stapling head assembly (600) may be more easily removed from the anatomical passageway without sticking to, or otherwise clinging to, recently captured tissue.

While in the current example, a resilient nub (662) and ledge (632) are used to retain staple driving body (660) at or near a distal-most position, any other suitable structures may be utilized as would be apparent to one skilled in the art in view of the teachings herein.

III. Exemplary Combinations

The following examples relate to various non-exhaustive ways in which the teachings herein may be combined or applied. The following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) an anvil defining a plurality of staple forming pockets; and (b) a stapling head assembly comprising: (i) a body, (ii) a coupling member configured to actuate relative to the body to thereby actuate the anvil relative to the body, (iii) a staple deck defining a plurality of staple openings, and (iv) a firing assembly configured to drive a plurality of staples against the staple forming pockets of the anvil, wherein the firing assembly comprises: (A) a proximal driving body slidably housed within the body, and (B) an array of discrete staple driving segments positioned distal to the proximal driving body and each having a free proximal end, wherein the proximal driving body is configured to simultaneously actuate the array of staple driving segments to drive the plurality of staples against the staple forming pockets of the anvil.

Example 2

The surgical stapling instrument of any one or more of the preceding Examples, wherein the staple deck further comprises a stop surface, wherein the stop surface is configured to engage a staple driving segment of the array of staple driving segments to prevent the staple driving segment from disassociating with the staple deck.

Example 3

The surgical stapling instrument of any one or more of the preceding Examples, wherein the staple driving segment of the array of staple driving segment further comprises a stop body configured to engage the stop surface of the staple deck.

Example 4

The surgical stapling instrument of any one or more of the preceding Examples, wherein each staple driving segment of the array of staple driving segments comprises a proximal surface configured to engage the proximal driving body.

Example 5

The surgical stapling instrument of any one or more of the preceding Examples, wherein each staple driving segment of the array of staple driving segments comprises a distal staple engagement surface configured to suitably engage a respective staple of the plurality of staples.

Example 6

The surgical stapling instrument of any one or more of the preceding Examples, wherein each staple driving segment of the array of staple driving segments is slidably housed within a respective staple opening.

Example 7

The surgical stapling instrument of any one or more of the preceding Examples, wherein each staple driving segment of the array of staple driving segments is configured to drive a respective staple out of the respective staple opening.

Example 8

The surgical stapling instrument of any one or more of the preceding Examples, wherein the plurality of staple openings comprises a first circumferential array of staple openings.

Example 9

The surgical stapling instrument of any one or more of the preceding Examples, wherein the plurality of staple openings comprises a second circumferential array of staple openings.

Example 10

The surgical stapling instrument of any one or more of the preceding Examples, wherein each staple driving segment of the plurality of staple driving segments comprises a retention feature configured to inhibit proximal movement of the staple driving segment.

Example 11

The surgical stapling instrument of any one or more of the preceding Examples, wherein the retention feature comprises a resilient nub.

Example 12

The surgical stapling instrument of any one or more of the preceding Examples, wherein the staple deck comprises a distally facing ledge configured to engage the resilient nub.

Example 13

The surgical stapling instrument of any one or more of the preceding Examples, wherein the anvil is configured to selectively attach and detach from the coupling member.

Example 14

The surgical stapling instrument of any one or more of the preceding Examples, further comprising a shaft assembly extending proximally from the stapling head assembly.

Example 15

The surgical stapling instrument of any one or more of the preceding Examples, further comprising a handle assembly attached to a proximal end of the shaft assembly.

Example 16

A surgical stapling instrument, comprising: (a) an anvil defining a plurality of staple forming pockets; and (b) a stapling head assembly comprising: (i) a body, (ii) a coupling member configured to actuate relative to the body to thereby actuate the anvil relative to the body, (iii) a staple deck defining a plurality of staple openings, wherein each staple opening in the plurality of staple openings contains a staple, and (iv) a firing assembly configured to drive a plurality of staples against the staple forming pockets of the anvil, wherein the firing assembly comprises: (A) a proximal driving body slidably housed within the body, wherein the proximal driving body comprises a plurality of pushing bodies located proximal relative to the plurality of staple openings, and (B) a plurality of staple driving bodies slidably contained within the plurality of staple openings, wherein the staple driving bodies extend proximally from the staple openings and are engaged with the pushing bodies such that the proximal driving body is configured to simultaneously fire the plurality of staple driving bodies, wherein the staple driving bodies are decoupled from one another such that the staple driving bodies are configured to be individually inserted within respective openings of the plurality of staple openings.

Example 17

The surgical stapling instrument of any one or more of the preceding Examples, wherein the plurality of staple driving bodies is disposed along an arched profile.

Example 18

The surgical stapling instrument of any one or more of the preceding Examples, wherein the plurality of staple driving bodies comprises a distal end configured to extend distally past the staple deck in response to distal actuation of the proximal driving body.

Example 19

The surgical stapling instrument of any one or more of the preceding Examples, wherein the coupling member comprises a trocar.

Example 20

A surgical stapling instrument, comprising: (a) an anvil defining a plurality of staple forming pockets; and (b) a stapling head assembly comprising: (i) a body, (ii) a coupling member configured to actuate relative to the body to thereby actuate the anvil relative to the body, (iii) a staple deck defining a plurality of staple openings, wherein the staple deck is fixed to the body, and (iv) a firing assembly configured to drive a plurality of staples against the staple forming pockets of the anvil, wherein the firing assembly comprises: (A) a proximal actuating body slidably housed within the body, wherein the proximal actuating body comprises a plurality of pushing bodies terminating proximal relative to the plurality of staple openings, and (B) an array of staple driving segments slidably contained within the plurality of staple openings, wherein the staple driving segments are decoupled from one another such that each staple driving segment of the array of staple driving segments are configured to be individually inserted into a respective opening of the plurality of staple openings, wherein the pushing bodies are configured to simultaneously actuate the staple driving segments.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical stapling instrument, comprising:
   (a) an anvil defining a plurality of staple forming pockets;
   (b) a stapling head assembly comprising:
      (i) a body,
      (ii) a coupling member configured to actuate relative to the body to thereby actuate the anvil relative to the body,
      (iii) a staple deck defining a plurality of staple openings, wherein the staple deck comprises a plurality of a stop surfaces, and
      (iv) a firing assembly configured to drive a plurality of staples against the staple forming pockets of the anvil, wherein the firing assembly comprises:
         (A) a proximal driving body slidably housed within the body, and
         (B) an array of discrete staple driving segments positioned distal to the proximal driving body and each having a free proximal end, wherein the proximal driving body is configured to simultaneously actuate the array of staple driving segments to drive the plurality of staples against the staple forming pockets of the anvil; wherein each stop surface of the plurality of stop surfaces is configured to inhibit a respective staple driving segment of the array of stapling driving segments from actuating distally past the staple deck along a common distal direction and thereby inhibit each staple driving segment of the array of staple driving segments from disassociating from the staple deck; and
   (c) a shaft assembly extending proximally from the stapling head assembly.

2. The surgical stapling instrument of claim 1, wherein at least one staple driving segment of the array of staple driving segments further comprises a stop body configured to engage a respective stop surface of the plurality of stop surfaces of the staple deck.

3. The surgical stapling instrument of claim 1, wherein each staple driving segment of the array of staple driving segments comprises a proximal surface configured to engage the proximal driving body.

4. The surgical stapling instrument of claim 3, wherein each staple driving segment of the array of staple driving segments comprises a distal staple engagement surface configured to suitably engage a respective staple of the plurality of staples.

5. The surgical stapling instrument of claim 1, wherein each staple driving segment of the array of staple driving segments is slidably housed within a respective staple opening.

6. The surgical stapling instrument of claim 5, wherein each staple driving segment of the array of staple driving segments is configured to drive a respective staple out of the respective staple opening.

7. The surgical stapling instrument of claim 1, wherein the plurality of staple openings comprises a first circumferential array of staple openings.

8. The surgical stapling instrument of claim 7, wherein the plurality of staple openings comprises a second circumferential array of staple openings.

9. The surgical stapling instrument of claim 1, wherein each staple driving segment of the plurality of staple driving segments comprises a retention feature configured to inhibit proximal movement of the staple driving segment.

10. The surgical stapling instrument of claim 9, wherein the retention feature comprises a resilient nub.

11. The surgical stapling instrument of claim 10, wherein the staple deck comprises a distally facing ledge configured to engage the resilient nub.

12. The surgical stapling instrument of claim 1, wherein the anvil is configured to selectively attach and detach from the coupling member.

13. The surgical stapling instrument of claim 1, further comprising a handle assembly attached to a proximal end of the shaft assembly.

14. A surgical stapling instrument, comprising:
(a) an anvil defining a plurality of staple forming pockets; and
(b) a stapling head assembly comprising:
  (i) a body,
  (ii) a coupling member configured to actuate relative to the body to thereby actuate the anvil relative to the body,
  (iii) a staple deck defining a plurality of staple openings, wherein each staple opening in the plurality of staple openings contains a staple, and
  (iv) a firing assembly configured to drive a plurality of staples against the staple forming pockets of the anvil, wherein the firing assembly comprises:
    (A) a proximal driving body slidably housed within the body, wherein the proximal driving body comprises a plurality of pushing bodies located proximal relative to the plurality of staple openings, and
    (B) a plurality of staple driving bodies slidably contained within the plurality of staple openings, wherein the staple driving bodies extend proximally from the staple openings and are engaged with the pushing bodies such that the proximal driving body is configured to simultaneously fire the plurality of staple driving bodies, wherein the staple driving bodies are decoupled from one another such that the staple driving bodies are configured to be individually inserted within respective openings of the plurality of staple openings.

15. The surgical stapling instrument of claim 14, wherein the plurality of staple driving bodies is disposed along an arched profile.

16. The surgical stapling instrument of claim 14, wherein the plurality of staple driving bodies comprises a distal end configured to extend distally past the staple deck in response to distal actuation of the proximal driving body.

17. The surgical stapling instrument of claim 14, wherein the coupling member comprises a trocar.

18. A surgical stapling instrument, comprising:
(a) an anvil defining a plurality of staple forming pockets; and
(b) a stapling head assembly comprising:
  (i) a body,
  (ii) a coupling member configured to actuate relative to the body to thereby actuate the anvil relative to the body,
  (iii) a staple deck defining a plurality of staple openings, wherein the staple deck is fixed to the body, and
  (iv) a firing assembly configured to drive a plurality of staples against the staple forming pockets of the anvil, wherein the firing assembly comprises:
    (A) a proximal actuating body slidably housed within the body, wherein the proximal actuating body comprises a plurality of pushing bodies terminating proximal relative to the plurality of staple openings, and
    (B) an array of staple driving segments slidably contained within the plurality of staple openings, wherein the staple driving segments are decoupled from one another such that each staple driving segment of the array of staple driving segments are configured to be individually inserted into a respective opening of the plurality of staple openings, wherein the pushing bodies are configured to simultaneously actuate the staple driving segments.

\* \* \* \* \*